(12) United States Patent
Jones et al.

(10) Patent No.: US 8,103,455 B2
(45) Date of Patent: Jan. 24, 2012

(54) METHOD OF ASSESSING THE PROLIFERATION OR DIFFERENTIATION BEHAVIOUR OF A POPULATION OF TARGET CELLS IN A BIOLOGICAL SYSTEM

(75) Inventors: Philip Howlett Jones, Cambridge (GB); Benjamin David Simons, Cambridge (GB)

(73) Assignee: Medical Research Council, London (GB)

( * ) Notice: Subject to any disclaimer, the term of this patent is extended or adjusted under 35 U.S.C. 154(b) by 734 days.

(21) Appl. No.: 12/281,740

(22) PCT Filed: Feb. 27, 2007

(86) PCT No.: PCT/GB2007/000675
§ 371 (c)(1), (2), (4) Date: Nov. 20, 2008

(87) PCT Pub. No.: WO2007/101979
PCT Pub. Date: Sep. 13, 2007

(65) Prior Publication Data
US 2011/0301864 A1    Dec. 8, 2011

Related U.S. Application Data

(60) Provisional application No. 60/780,356, filed on Mar. 9, 2006.

(30) Foreign Application Priority Data

Mar. 9, 2006  (GB) .................................. 0604819.3

(51) Int. Cl.
*G01N 33/48* (2006.01)
(52) U.S. Cl. ......................................................... 702/19
(58) Field of Classification Search .................. None
See application file for complete search history.

(56) References Cited

OTHER PUBLICATIONS

Kemp et al., "Elimination of background recombination: somatic induction of Cre by combined transcriptional regulation and hormone binding affinity." Nucleic Acids Research, vol. 32, No. 11. Copyright Oxford University Press 2004.
Srinivas et al., "Cre reporter strains produced by targeted insertion of EFP and ECFP into ROSA26 locus." BMC Development Biology, vol. 1, No. 4, 2001.
Sebok et al., "Effect of Fumaric Acid, Its Dimethylester, and Topical Antipsoriatic Drugs on Epidermal Differentiation in the Mouse Tail Model." Skin Pharmacol, 1996, pp. 99-103.
Loeffler et al., Epidermal cell proliferation II. A comprehensive mathematical model of cell proliferation and migration in the basal layer predicts some unusual properties of epidermal stem cells. Virchows Arch B, vol. 53, 1987, pp. 286-300.
Clayton et al., "Applying a new paradigm of epidermal homeostasis to analyse the clonal evolution of cancer." NCRI Cancer Conference 8, Oct. 11, 2006.
Clayton et al., "A single type of progenitor cell maintains normal epdiermis." Nature, Vold. 446, Mar. 8, 2007.

*Primary Examiner* — Jason Sims
(74) *Attorney, Agent, or Firm* — McAndrews, Held & Malloy Ltd.

(57) ABSTRACT

The invention relates to a method of assessing the proliferation or differentiation behavior of a population of target cells in a biological system, said method comprising the steps of; [a] measuring the value of at least one proliferation characteristic of said cells at least one time point t, wherein said proliferation characteristic is the clone size distribution; [b] comparing the clone size distribution measured in [a] to a reference clone size distribution at a corresponding time point t predicted or described by the equation; wherein a difference between the measured clone size distribution of [a] and the predicted or described clone size distribution of [b] indicates an altered proliferation or differentiation behavior of said cells. The invention further relates to methods involving assessing the scaling form of the above behaviors, values of the parameters, and inferring effects on cell proliferation and/or differentiation therefrom.

24 Claims, 19 Drawing Sheets

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 1
cgtactgacg gtgggagaat                                             20

<210> SEQ ID NO 2
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 2
cccggcaaaa caggtagtta                                             20

METHOD OF ASSESSING THE PROLIFERATION OR DIFFERENTIATION BEHAVIOUR OF A POPULATION OF TARGET CELLS IN A BIOLOGICAL SYSTEM

The present application is filed pursuant to 35 U.S.C. 371 as a U.S. National Phase application of International Patent Application No. PCT/GB2007/000675, which was filed Feb. 27, 2007, claiming the benefit of priority to British Patent Application No. GB 0604819.3, which was filed on Mar. 9, 2006 and U.S. Patent Application No. 60/780,356, which was filed on Mar. 9, 2006. The entire text of the aforementioned applications is incorporated herein by reference in its entirety.

This invention relates to methods of analysing and predicting cell growth behaviour such as proliferation and differentiation, and in particular, to methods and materials for assessing changes in the growth behaviour of cells. This may be useful, for example, in identifying agents which alter growth behaviour, for example in carcinogenicity or toxicity screening and the development of cancer therapeutics.

The epidermis is organised into hair follicles interspersed with interfollicular epidermis (IFE) which consists of layers of keratinocytes (FIG. 1).[6] In IFE, proliferating cells are found in the basal cell layer; on commitment to terminal differentiation, basal cells exit the cell cycle and subsequently migrate into the suprabasal cell layers. How epidermal progenitor cells (EPCs) function to support IFE remains unclear. It has long been held that cells lost from adult mammalian epithelia are replaced by the continuous proliferation of self-renewing stem cells (SC), which generate differentiated cells via an intermediate population of short-lived transit amplifying (TA) cells.[1-4] The epidermis is thought to be organised into hexagonal shaped epidermal proliferative units (EPUs), each maintained by a single stem cell and its TA cell progeny.[5]

Progenitor cells which are capable of generating both hair follicles and IFE lie in the hair follicle bulge, but these cells appear to play no role in maintaining normal IFE.[7-11] Label retaining studies show IFE contains slowly cycling basal cells which, according to the SC/TA model, represent SCs supporting an overlying EPU.[5,12]

Prior art techniques for modelling cell proliferation and differentiation behaviour suffer from problems of complexity and are often unwieldy and difficult to apply across different systems. Furthermore, prior art models frequently involve attributing various behaviours or involvement to multiple cell classes including stem cells which can complicate matters further. The closest prior art to the present invention might be wound healing based models which seek to remove or damage tissue and then study its regeneration or repair. Clearly such studies suffer from problems associated with the study of artificial systems such as wound healing. Moreover, the involvement or role of cells such as stem cells in steady state behaviour is incompletely understood in the art, making it inherently difficult to model the biological systems. The present invention seeks to overcome problem(s) associated with the prior art.

SUMMARY OF THE INVENTION

The present inventors have recognised that the proliferation of cells in certain biological systems surprisingly involves a single type of progenitor cell and can be described by a simple mathematical model. This model allows changes in the growth behaviour of cells to be identified at an early stage and has a range of applications, for example in carcinogenicity or toxicity screening, the development of cancer therapeutics, and related areas.

The present inventors have derived mathematical models of tissue homeostasis. Prior art models have necessarily been very complicated, and difficult to rely on. In contrast, through a process of observation and experimentation, the present inventors have derived a surprisingly simple way of relating the various parameters involved in cell proliferation and differentiation in order to arrive at a robust predictive and descriptive model of tissue, homeostasis.

One of the most striking observations which the inventors have made is that one rate limiting process can determine the whole model. In particular, clonal size distributions have been shown to vary in a predictable manner with time. Moreover, plots of average clone size versus time can be seen to be straight lines, again supporting a direct proportional relationship between the clone size and time.

In addition to the underlying "master equation" governing the proliferative and differentiation behaviour, it has been surprisingly shown that the results and predictions can be reliably scaled to different cell populations and different time points. Indeed, this reliable scaling is a signature of the type of cell dynamics described herein.

In summary, the invention is based upon the surprising findings that a single rate limiting process can determine the model of tissue homeostasis, and the striking simplicity of the mathematical relationship which the inventors have derived. Indeed, the models presented herein are the only plausible models which fit the observations. The invention is based upon these surprising findings.

Thus, in one aspect the invention provides a method of assessing the proliferation or differentiation behaviour of a population of target cells in a biological system, said method comprising the steps of;

[a] measuring the value of at least one proliferation characteristic of said cells at least one time point t, wherein said proliferation characteristic is the clone size distribution;

[b] comparing the clone size distribution measured in [a] to a reference clone size distribution at a corresponding time point t predicted or described by the equation;

$$\frac{dP_{n_A,n_B}}{dt} = \lambda\{r[(n_A-1)P_{n_A-1,n_B} + (n_A+1)p_{n_A+1,n_B-2}] + (1-2r)n_A P_{n_A,n_B-1} - n_A P_{n_A,n_B}\} + \Gamma[(n_B+1)P_{n_A,n_B+1} - n_B P_{n_A,n_B}]$$

wherein a difference between the measured clone size distribution of [a] and the predicted or described clone size distribution of [b] indicates an altered proliferation or differentiation behaviour of said cells.

Preferably said measurement and comparison steps are performed for two or more time points.

Preferably the at least one proliferation characteristic of the target cells is measured at two or more time points following said labelling. Although t=0 typically refers to the time of labelling, in embodiments where interventional labelling is not required then t=0 can be picked according to the needs of the operator, for example the start day of the study. Clearly, the timing of any treatment of the target cells will be separately monitored and may or may not coincide with t=0. Indeed, it may be advantageous to ensure that any treatment takes place only after the initial transient period during which the label becomes robustly detectable (typically two weeks when using the preferred labelling techniques discussed herein), as a more reliable reference or control population may this way be established, and any possible effects of treatment(s) on cell labelling can be eliminated from the study.

A 'population of target cells' may refer not just to a single clone lineage but to a plurality of clones together making up the population of target cells. Such clones may be in the same biological system or may be in a plurality of corresponding biological systems. For example, the population of target cells may be made up of a number of clones, which clones may be within different test animals. For example a population of target cells may comprise 30 clones, 10 of which are each within 3 separate animals. Any other suitable breakdown of clone numbers may be chosen by the operator. The key point is that the clones making up the population from which a clone size distribution is produced must come from equivalent systems e.g. in vivo on the same genetic background or in culture under similar conditions or in otherwise comparable settings in accordance with good scientific practice. The principle is that the population of cells at different time points may be comprised of different actual cells since as will be apparent to the skilled reader, counting of the cells/clones often involves destruction of the cells and removal from incubation so those actual individual cells typically cannot be returned to culture to form part of a count at a future time point. Thus, it is important that the cells counted at any given time point are equivalent to the cells counted at other time points, but clearly those cells counted at subsequent time points will not actually be the specific individual cells counted at the earlier time points since it is a population/cohort which is being analysed. Of course, if the clones can be counted non-destructively then the invention may be practised on a single cohort of cells which are individually counted and recounted at subsequent time points. However, in practical terms, the most common applications of the invention will be as set out above (population/cohort counting of equivalent populations or clones at the specific time points).

Preferably the clone size is determined as the number of cells in the clone.

Preferably the biological system is a tissue. Preferably the tissue is epidermis.

The population of target cells may be in an animal, preferably a non-human test animal.

Preferably the population of cells consists of one or more clonal cell lineage(s).

Preferably said target cells are labelled with an inheritable marker.

Preferably fewer than 1 in 27 cells in the system are labelled as target cells. This has the advantage that the individual clones are likely to be well separated the therefore easier to follow as independent clones, and avoids problems of clones merging as they expand, or neighbouring cells being marked and giving rise to mixed clones appearing as a single clone. Generally lower marking ratios are preferred for these reasons as discussed below.

Preferably the target cells are labelled by expression of a marker gene.

In another aspect, the invention provides a method as described above wherein the value of at least one proliferation characteristic is measured by
(i) providing a test animal comprising a marker gene,
(ii) inducing inheritable activation of said marker in at least one cell of said test animal, wherein inheritable activation is induced in fewer than 1 in 27 cells in the tissue of interest,
(iii) incubating the test animal,
(iv) visualising those clonal cells which express the marker gene as a result of the inheritable activation, and
(v) measuring the value of the at least one proliferation characteristic of the visualised clonal cells.

Preferably the visualisation is by confocal microscopy.

The target cells may be treated with a test compound before the at least one proliferation characteristic is measured. Preferably the target cells are comprised in the epidermis of a test animal and test compound is topically administered to the epidermis of the test animal. Topical administration may be by any suitable method such as 'painting' the material onto the tissue, or may be by injection, spraying, cream, ointment, particle gun, dipping, or application of a patch or slow release device comprising the compound or any other suitable means.

Preferably a difference in the proliferation or differentiation characteristic(s) of the treated target cells relative to the reference cells is indicative that the test compound affects cell proliferation or differentiation behaviour.

In another aspect, the invention provides a method as described above comprising expressing a test gene in the target cells before the at least one proliferation characteristic is measured. Increased proliferative behaviour of the target cells expressing the test gene is indicative that the test gene is an oncogene.

In another aspect, the invention provides a method as described above comprising expressing a gene which changes growth behaviour in the target cells and treating the target cells expressing said gene with a test compound before the at least one proliferation characteristic is measured. A reduction or enhancement of the changes in the growth behaviour induced by expression of said gene in the treated cells is indicative that the test compound affects cell growth behaviour. When expression of said gene increases proliferation in the target cells, then a reduction or abrogation of said proliferation in the treated cells is indicative that the test compound is a candidate cosmetic agent or anti-cancer therapeutic agent.

Preferably the target cells are deficient in a tumour suppressor gene such as p53.

In another aspect, the invention provides a method as described above wherein the reference clone size distribution of (b) is a clone size distribution at a second time point t2 for a population of said target cells, said method further comprising
(c) resealing the clone size distributions to the same time co-ordinate; and
(d) comparing the curve shapes of (c);
wherein if said curve shapes are different, then the proliferation or differentiation behaviour of the cells is assessed to be abnormal.

In another aspect, the invention provides a method as described above further comprising determining whether the proliferation or differentiation behaviour of the cells complies with the scaling form:

$$P^{pers}_{n>0}(t) = \frac{\tau}{t} f(n\tau/t) \tag{1}$$

wherein if said proliferation or differentiation behaviour conforms to said scaling form, then the proliferation or differentiation behaviour of the cells is assessed to be normal, and wherein if said proliferation or differentiation behaviour does not conform to said scaling form, then the proliferation or differentiation behaviour of the cells is assessed to be abnormal. Preferably said method further comprises comparing at least one further parameter predicted or described by application of said equation to said target cell population with at least one further parameter predicted or described by application of said equation to said reference cell population; and identifying parameters which are altered in said target cell population, thereby characterising the changes in the proliferation or differentiation behaviour of the target cells.

DETAILED DESCRIPTION OF THE INVENTION

As noted above, the present inventors have recognised that the proliferation of cells in certain biological systems does not involve stem cells and can be described by a simple mathematical model. Indeed, with respect to the involvement of stem cells, in certain systems investigated to date, it appears that proliferation involves one progenitor cell compartment.

Clone Size

The clone size is determined by assessing the magnitude of the particular clone being studied. This may be measured by any suitable means. For example, the total physical size of the clone may be measured. This may be by estimation of characteristics such as the mass or the volume of the clone being studied. In another embodiment, the clone size may be assessed as the diameter of the particular clone being studied, which is particularly preferred when the clone is located in back skin. In this embodiment, preferably the diameter is taken as the average diameter. This can be particularly important when the clone is other than circular. Alternatively, the clone size may be assessed by measuring the two dimensional area occupied by the clone. In a preferred embodiment, the clone size means the total number of cells in the clone. Preferably, the clone size is the total number of nucleated cells in the clone.

In order to produce a meaningful clone size distribution, a number of clones must be measured to produce a number of clone size data points for a given time point. Preferably a distribution comprises at least 30 individual clone sizes, preferably at least 100 individual clone sizes. An advantage of larger numbers of clone sizes is improved accuracy of the clone size distribution.

Biological Systems

The invention finds particular application in squamous tissue such as squamous epidermis, in particular stratified squamous tissue such as stratified squamous epidermis.

The biological system may be a tissue. The tissue may be a stratified tissue which comprises a basal layer and one or more supra-basal layers. The tissue may be epidermis.

When the target cells comprise cycling and non-cycling cell, the cycling cells may be maintained in a basal layer and the non-cycling cells migrate out of the basal layer.

Preferably the value of the at least one proliferation characteristic is measured in a sample of the tissue. Preferably this measurement is in vitro.

Preferably the population of target cells is in, or was in, a non-human test animal.

One aspect of the invention provides a method of assessing changes in the growth behaviour, for example changes in proliferation and/or differentiation, of target cells in a population, the method including the steps of:
a) measuring the value of at least one proliferation characteristic of said cells;
b) comparing the measured value with the value predicted for said characteristic for normal cells in the population by a model of cell growth behaviour,
   wherein said model of cell growth behaviour requires a parent cycling cell to divide into either 1) two cycling daughter cells, 2) a cycling and a non-cycling daughter cell or 3) two non-cycling daughter cells; and none of the cells in said population is a stem cell,
c) determining the likelihood of changes in the growth behaviour of said cells from the difference in said measured and predicted values.

Changes in growth behaviour of a target cell may include changes or alterations in proliferation and/or differentiation, for example relative to controls (i.e. normal cells). A cell with altered growth behaviour may, for example, have abnormal proliferation and/or differentiation.

The cell population containing the target cells may be within a tissue. Preferably, the tissue comprises more than one region or layer and may, for example, be a stratified tissue which comprises a basal layer and one or more supra-basal layers. Stratified tissues include stratified squamous tissue, such as epithelial tissue, oesophageal or cervical tissue. In some preferred embodiments, the stratified squamous tissue is epidermis, which is amenable to confocal imaging and allows 3-D imaging to conveniently trace cells derived from a single clone. The tissue may be skin such as dorsal skin such as back skin or peripheral skin such as tail skin, or may be oesophagus or ear tissue. Preferably the tissue is squamous epithelium such as skin, preferably peripheral skin such as tail skin.

In some embodiments, the tissue comprising the target cells may be in an animal or, more preferably, in a sample which is obtained from an animal, for example a tissue biopsy. Suitable animals may include humans and non-human animals in particular mammals, for example rodents such as mice. The methods described herein allow the numbers of animals which are required to recognise an effect on cell growth behaviour to be reduced. This is due at least in part to the titration of the marking system to mark cells which are (on average) spatially well separated in the biological system of interest. In this way, when the clones are in an animal, multiple clones per animal can be studied. This has the advantage of reducing the number of animals which are needed in order to obtain sufficient clones for a robust study of a particular treatment or genetic makeup. Indeed, for topically applied treatments, it may even be possible to study multiple treatments per animal, each treatment including multiple clones, thereby still further reducing the number of animals required for each condition.

In other embodiments, the stratified tissue may be an artificial tissue model system, such as organotypic keratinocyte cultures.

The cycling cells may be maintained in a particular region or layer in the tissue, for example a basal layer, and the non-cycling cells may migrate out of the region or layer containing the cycling cells, for example, into one or more supra-basal layers. In stratified squamous tissue such as epithelium, cell may eventually be shed from the tissue surface.

Cycling cells may be described herein as 'A cells', non-cycling basal cells as 'B cells' and non-cycling cells in the supra-basal layer as 'C cells'. The A cells may divide into two daughter A cells at rate $\lambda_{AA}$ and into two daughter B cells may be termed $\lambda_{BB}$ and may divide asymmetrically into an A and a B cell at a rate termed $\lambda_{AB}$. The rate of migration into the supra-basal layer may termed $\lambda_{BC}$.

Cycling cells (A cells) are cells which are actively proliferating and capable of mitosis and cell division. Cycling cells are not immortal as they are capable of division into two non-cycling cells which proceed through the differentiation pathway and are therefore distinct from stem cells.

Non-cycling cells (B and C cells) are cells which are not actively proliferating and are not capable of further mitosis and cell division. Non-cycling cells may be partly or terminally differentiated.

Cycling and non-cycling cells may be identified and distinguished using a range of known cell markers, including, for example, Ki67, CDC6 and bromodeoxyuridine staining. Antibodies which specifically bind to these markers are commercially available.

Normal cells are non-transformed (i.e. non-cancer) cells whose cell cycle mechanisms are fully functional and which are capable of terminal differentiation and apoptosis, for example in response to cell signalling pathways regulating tissue homeostasis.

A population of normal cells is generally in a steady state, such that the rate of generation of cells by cell division is equal to the rate of cell loss, for example by migration. The number of cells per unit area and the proportion of cycling cells over time may remain constant in a steady state population. Therefore, for normal cell proliferation, the rate of division to two cycling daughter cells ($\lambda_{AA}$) may be assumed to be equal to the rate of division to two non-cycling daughter cells ($\lambda_{BB}$). Thus, preferably the rate of division to two cycling daughter cells is assumed to be equal to the rate of division to two non-cycling daughter cells for normal cell proliferation. Cells with altered growth behaviour, for example cells in which proliferation and/or differentiation is abnormal, may not be in a steady state and these rates may not be equal.

Suitable target cells in a population may consist of one or more clonal cell lines, preferably one or more discrete or distinguishable clonal lines. A clonal cell line is a group or family of cells which are all descended from a single common ancestor cell. Following division and/or differentiation, there will typically be numerous cells which derive from the initial single cell. Due to differentiation, some or all of these cells may not be identical and may be distinguishable from each other (e.g. morphologically or by profiling of gene expression). Practically, cells may be regarded as descended from a common ancestor if they are labelled and spatially clustered consistent with this. Labelled cells may, for example, express an inheritable marker whose activation was induced in the parent cell. All descendents of the parent cell will then be labelled by the expression of the inheritable marker.

Clonal lines within a population of cells, for example in a tissue, are preferably distinguishable from other clonal lines within the population, for example by being labelled and preferably spatially separated.

The fate of a clonal cell line may be determined over time, for example, changes in the number or type of cells in the clonal cell line may be determined over time. In some embodiments, the fate of multiple clonal cell lines within a single population may be determined over time.

Contrary to the stem cell based models described previously, the cell growth behaviour model described herein predicts that the size distribution of the one or more clonal cell lines will increase with time. This is confirmed in the experimental data set out below.

Suitable proliferation characteristics which may be measured in the target cells in order to determine the likelihood of changes in the growth behaviour of the target cells using the model described above may include the total number of cells in a clonal cell line, the number of basal cells in a clonal cell line, clonal size distribution, the proportion of cycling and non-cycling cells in the clonal cell line, the proportion of cycling basal cells in the clonal cell line, ratio of different types of cell (e.g. cycling:non-cycling), numbers of different types of cell, cluster size distribution of one or more types of cell, rates of asymmetric division and/or rates of symmetric division.

The target cells may be eukaryotic cells, preferably mammalian cells, for example rodent cells, such as mice cells, or primate cells, such as human cells.

In the murine epidermis, particularly tail epidermis, the data set out herein shows that the probability of asymmetric cell division (pAD) is about 0.84. In other words, 84% of cell division in the murine epidermis is asymmetric and 16% is symmetric (i.e. 8% producing two cycling (A) daughter cells and 8% producing two non-cycling (B) daughter cells). These figures are applied and illustrated in connection with murine tail epidermis. It should be noted that the model presented herein is the same for other mammalian tissues, particularly when in steady state. Of course the precise values of these constants may be different in other tissues—this may be easily checked by the operator either by reference or by observation.

The value of the at least one proliferation characteristic may be determined at one or more time points. In some embodiments, readings may be taken of the target cells at two or more time points in order to produce the value for the proliferation characteristic.

Mathematical Model

It is a feature of the model of the present invention that clone size expansion due to factors such as tissue growth or cell death have been ruled out from affecting the model. For example, one hypothesis regarding clonal expansion may involve a cell adjacent to the clone of interest dying, which could lead to a marked cell of the clone of interest dividing in order to replace its dead neighbour. The mathematical model of the present invention benefits from the fact that at this type of influence has been found not to adversely influence the analysis or predictions made.

The model of cell growth behaviour which is used to predict the value of the proliferation characteristic for normal cells may be defined by the parameters of: the overall division rate of cycling cells ($\lambda$); the probability that the division is asymmetric ($p_{AD}$); and the rate of transfer of non cycling cells from the basal to the suprabasal layer ($\Gamma$).

Assuming that the rates of symmetric cell division to cycling and non-cycling daughter cells are identical for normal cells, these parameters may then be related by the equation:

$$\frac{d}{dt}P_{mn} = \lambda\left\{\frac{1}{2}(1-p_{AD})[(m-1)P_{m-1,n} + (m+1)P_{m+1,n-2}] + p_{AD}mP_{mn-1} - mP_{mn}\right\} + \Gamma[(n+1)P_{mn+1} - nP_{mn}]$$

where $P_{mn}(t)$ is the probability that the cells consist of m cycling cells and n non-cycling cells after a time t after induction and, $P_{mn}(0) = n\delta_{m1}\delta_{n0} + (1-n)\delta_{m0}\delta_{n1}$.

In some embodiments, changes in the cell growth behaviour may include changes in the ratio of $\lambda_{AA}:\lambda_{BB}$. For example, whilst in normal cell proliferation and differentiation, $\lambda_{AA}:\lambda_{BB}$ may equal 1, $\lambda_{AA}:\lambda_{BB}$ may be found to be greater than 1 or less than 1 in the target cells. This may be indicative of either excessive proliferation, which may, for example, be indicative of cancer, or proliferation which may be insufficient for tissue homeostasis.

The same equation may be conveniently written in the following form: Defining $P_{n_A,n_B}(t)$ as the probability that a labelled clone involves $n_A$ A-type and $n_B$ B-type EPCs at time t after induction, its time-evolution is governed by the Master Equation:

$$\frac{dP_{n_A,n_B}}{dt} =$$
$$\lambda\{r[(n_A-1)P_{n_A-1,n_B} + (n_A+1)P_{n_A+1,n_B-2}] + (1-2r)n_A P_{n_A,n_B-1} - n_A P_{n_A,n_B}\} + \Gamma[(n_B+1)P_{n_A,n_B+1} - n_B P_{n_A,n_B}]$$

subject to the initial condition $P_{n_A,n_B}(0) = \rho\delta_{n_A,1}\delta_{n_B,0} + (1-\rho)\delta_{n_A,0}\delta_{n_B,1}$.

This is clearly the same as the equation presented above, with $(1-2r) = P_{AD}$ and with $n_A = m$ and with $n_B = n$ and thus $n_A, n_B = m, n$. For convenience the methods of the invention preferably refer to this 'Master Equation'.

Values for these or other, alternative parameters may be determined by fitting the model to data derived for normal cell growth behaviour (i.e. cells which proliferate and differentiate normally). For example, a method may comprise measuring the values of one or more proliferation characteristics of normal cells, preferably two or more proliferation characteristics, and fitting the parameters to the measured values.

In some embodiments, the values of the one or more proliferation characteristics of normal cells may be measured at different times and the parameters fitted to the evolution of said value over time.

A method may comprise measuring the values of more than one proliferation characteristics of the cells.

The error bounds on the model for normal cell growth behaviour may be determined. These may be derived from the error bounds of the measured value of the proliferation characteristic of normal cells. These may be expressed by error bounds in the fitted values of the parameters.

Changes in the cell growth behaviour, for example the proliferation and/or differentiation, of the target cells may be identified, or the likelihood that the growth behaviour of the target cells is changed or altered relative to normal cell growth behaviour may be determined on the basis of the difference between the measured value of the proliferation characteristic and the value predicted for that proliferation characteristic for normal cell growth behaviour by the model, and the relationship between that measured value and the error bounds of the model.

The changes in cell growth behaviour, for example changes in proliferation and/or differentiation, may be characterised by determining the values of the parameters in the cell growth behaviour model which are required to describe the altered growth behaviour of the target cells. A method may comprise producing a model which describes the altered growth behaviour by fitting the cell proliferation model described above to the measured value of the at least one proliferation characteristic of the target cells by adjusting the parameters and/or assumptions which are used to characterise the growth behaviour of normal cells, thereby obtaining a cell growth behaviour model with adjusted parameters and/or assumptions which describes the altered growth behaviour.

By "fitting", is meant determining by automatic or semi-automatic means, values for the parameters in the cell growth behaviour model which allow the model to predict a value for the proliferation characteristic which corresponds to the measured value for that characteristic. Various computer-based methods for fitting are known in the art.

The parameters of the model describing altered cell growth behaviour may be compared with the parameters of the model describing normal cell growth behaviour and the amount or extent of alteration of the parameters in the altered growth model identified. This allows the changes in the cell growth behaviour to be identified and/or characterised.

Scaling

As noted above, it is a key feature of the models presented herein that they are readily scalable to different time points or different populations of cells. It is a core advantage of the scaling embodiments that abnormally proliferating/differentiating cells (such as pre-cancerous or cancerous cells) display a different scaling/signature to normal cells. In the simplest possible terms, if the scaling model is violated, then the cells are exhibiting abnormal proliferation or differentiation characteristics.

In more detail, scaling means that the probability distribution function has a scaling form. According to the present invention, the distribution of clones of a particular size at a particular time (the 'curve') is a function of the clone size, n. At different times (t), the curves will be different. Obeying scaling means that, given a curve at a particular time point (t1), the curves for any other time point (t2, t3, etc) will be fundamentally the same i.e. the same shape/curve. This can be easily verified or tested to determine if a particular system obeys scaling; to test it, the data from a first time (t) is taken and the time co-ordinate is resealed to a different time (t1). It is then determined by comparison whether or not the curves from the different time points 'collapse' or 'rescale' to the same shape curve. If they do, then the system is said to obey scaling or be scalable/have a scaling form (i.e. to concur with the scaling model). For an illustration of this, reference is made to FIG. 17a which is described in more detail in the examples section.

In more details, to identify the scaling behaviour, we define the clone-size distribution $P_n(t)$, describing the probability that a labelled progenitor cell develops into a clone with a total of n basal-layer cells at time t after induction. From this we can define the distribution of 'persisting' clones, that is, the distribution of labelled clones containing at least one basal-layer cell:

$$P_{n>0}^{pers}(t) \equiv \frac{P_n(t)}{1-P_0(t)}$$

With this definition, we show that (FIG. 17a and below), after an initial transient behaviour, the observed clone-size distributions are compatible with the simple scaling form:

$$P_{n>0}^{pers}(t) = \frac{\tau}{t}f(n\tau/t) \qquad (1)$$

where τ denotes some constant timescale.

This scaling test emphasises a key surprising finding of the present inventors, that the underlying dynamics of the model are strikingly simple. Furthermore, this scaling enables methods of distinguishing abnormal from normal cell behaviour, for example it allows mere acceleration of natural cell dynamics (e.g. ATRA treatment) to be distinguished from abnormal behaviour such as cancerous or precancerous growth. Furthermore, this scaling behaviour is characteristic of a steady state system; if the observed data do not scale, then it is an indication that the system is not in the steady state e.g. there may be a skew towards cell loss or cell gain or other imbalance which does not permit scaling to be followed.

If the proliferation or differentiation behaviour of the cells does not concur with the scaling model, then this may lead to ulceration (in the case of e.g. cellular loss or reduced proliferation or inappropriate differentiation); by contrast, failure to concur with the scaling model may alternatively be an indication that the cells are pre-cancerous or cancerous (in the case of e.g. over-accumulation or inappropriate exponential growth). Distinguishing these two possible inferences from a lack of conformity to the scaling model may be easily accomplished by using the master equation to infer parameters of the abnormal cell behaviour e.g. to determine whether cells are being lost (ulcerative) or gained (cancerous/precancerous) relative to the steady state or reference population; derivation of parameters using the master equation is described herein.

With regard to the study of test compounds, if those compounds are benign, then the cell proliferation or differentiation behaviour should obey the ordinary model given above in the master equation. If this is the case, then that model can be used to directly infer changes in cell division rates or other properties of their proliferative or differentiation behaviour such as the proportion of symmetric/asymmetric division. However, if the dynamics do not fit with that model and do not have a scaling form, then their behaviour is indicated as abnormal, whether that be cancerous or ulcerative in outcome.

Thus, when it is confirmed that the cell dynamics do conform to the scaling, then an additional advantage of the invention is that the other parameters can be derived from the equation, thereby usefully providing descriptions of the properties of cell kinetics in that system. Examples of the parameters which may be derived from the master equation once it has been confirmed that the system is scalable are the rates of cell division, and/or the channelling of cell division (i.e. the rate of asymmetric division versus the rate of symmetric division).

It should be noted that in the case of certain test systems, for example with very young mice if mouse skin epidermis is the biological system, there may be an initial expansion period before scaling or signature studies are possible. Nevertheless, after approximately 10 or 11 weeks the clone size distribution should conform to the scaling form. This can be caused by the system needing to reach a steady state, and the effect of fluctuations on small clone sizes (e.g. one or two cell clones) contributing 'noise'. Even in this initial transient period, the cell dynamics should follow the master equation. Starting with single-cell clones at induction, advantageously even the initial cell behaviour is described implicitly and in full by the master equation, before scaling behaviour sets in. The time to reach the scaling behaviour will vary according to the physical parameters of the system—mathematically it is set by $1/r\lambda$. In any case, we provide a complete description through the master equation. The application of scaling is discussed in more detail herein.

The only significant 'transient' period from a practical point of view depends upon the marking system used. In this regard, when the marking system is the preferred $Ahcre^{ERT}/R26^{EYFP/wt}$ system, then the 'transient period' is approximately two weeks. This two weeks is the amount of time it takes for each of the induced cells to express the marker to a threshold level for robust and reliable detection. Studies performed before the marker expression has passed this threshold risk missing induced cells at early time points due to the cells not being visualised. Clearly, the particular duration of this transient window allowing marker expression to reach the required level may vary from system to system, or according to the detection apparatus or other factors. It is well within the abilities of the person skilled in the art to observe when the marker has become reliably detectable and to work the invention with regard to this factor.

Notwithstanding the above advantages which can be derived from a steady state system which is obeying the scaling equation, the main advantage of the invention is to allow a decision to be taken whether or not cell dynamics do or do not conform to the provided model. In short, if the kinetics do not conform to the model of the invention, this is typically a negative indication for the particular treatment, compound or gene being studied. The failure to conform is a strong indication that the system is no longer obeying the simple cell kinetics. Once the system is no longer obeying the cell kinetics described herein, there are two principal inferences;

1. The compound of treatment is a non-carcinogenic compound or treatment, but may have other effects such as promotion of differentiation or anti-proliferative effect. This is likely to ultimately cause ulceration. The underlying mechanism may vary. For example, there may be an anomalously rapid loss of surviving clones. Furthermore, there is likely to be an anomalously smaller average clone size. Whatever the underlying reasons, typically this observation is indicative of an overall tendency towards loss of cells, and hence ulceration.

2. The compound or treatment is a carcinogen or carcinogenic. This will ultimately lead to tumours or non tumour cancers. The characteristics of the cells under these conditions are typically an emergence of exponential growth of clones (e.g. exponential increase of clone sizes). This is a typical signature of a carcinogen or carcinogenic treatment.

Single Time Points

When studying the cell dynamics using the equation presented herein, one time point may be enough to provide information, depending on the specific needs of the operator. However, of course it must be borne in mind that for scaling/signature analysis, it is essential to have more than one time point. Clearly, the scaling/signature analysis cannot be performed unless more than one time point data are provided.

For single time point embodiments, the input is preferably the clone size distribution. For example, this may be the number of cells in the clone, or for example may be the number of proliferating cells. Nevertheless, the dynamics are then compared to the master equation. If they fit the predictions of the master equation, the conclusion may be that the treatment or compound is benign. This does not necessarily imply that there is no effect, for example on the rate of cell division. Indeed, ATRA application is benign. However, ATRA application did in fact have an effect—the effect was to speed up the whole process. However, the whole process still fitted the dynamics described by the main equation—ATRA simply accelerated them. In terms of the mechanism, ATRA actually increased differentiation which led to a corresponding increase of proliferation as compensation. However, the key point is that the dynamics of cell proliferation and differentiation following ATRA treatment still fitted the master equation presented herein. From that point, it was then possible to use that equation to derive the other parameters such as the rate of cell proliferation (cell division) and therefore to better understand the nature of the benign ATRA treatment.

ATRA treatment is particularly useful in accelerating the studies performed in accordance with the present invention, since the overall effect is that the number of cell divisions across a particular time period is greatly increased, thereby simulating the maintenance of the homeostatic tissue for a far greater period of time than the time period across which the experiment is actually conducted.

Multi-Point Analysis

In another aspect, the invention provides a method of assessing the proliferation or differentiation behaviour of a population of target cells in a biological system, said method comprising (a) compiling a clone size distribution at a first time (t1) for a population of said target cells;
(b) compiling a clone size distribution at a second time (t2) for a population of said target cells;
(c) rescaling the clone size distributions to the same time co-ordinate; and
(d) comparing the curve shapes of (c);
wherein if said curve shapes are different (e.g. dissimilar or not substantially the same), then the proliferation or differentiation behaviour of the cells is assessed to be abnormal.

In more detail, if said curve shapes are substantially the same, then the proliferation or differentiation behaviour of the cells is assessed to be normal, and if said curve shapes are dissimilar, then the proliferation or differentiation behaviour of the cells is assessed to be abnormal Of course in certain embodiments the kinetics of the proliferation or differentiation behaviour might be normal i.e. balanced or steady-state, but the underlying rate of cell division might vary e.g. as observed in response to ATRA treatment where kinetics and steady state are normal but an accelerated proliferation/differentiation can be distinguished by inference of said parameters from the master equation as taught herein. Thus, in a preferred embodiment, first the scaling is tested and then the parameters described or predicted by the master equation are also compared to provide a multi-part analysis of cell proliferation or differentiation behaviour.

Preferably said method further comprises determining whether the proliferation or differentiation behaviour of the cells complies with the scaling form:

$$P_{n>0}^{pers}(t) = \frac{\tau}{t} f(n\tau/t) \quad (1)$$

wherein if said proliferation or differentiation behaviour conforms to said scaling form, then the proliferation or differentiation behaviour of the cells is assessed to be normal, and wherein if said proliferation or differentiation behaviour does not conform to said scaling form, then the proliferation or differentiation behaviour of the cells is assessed to be abnormal.

In another aspect, the invention provides a method of assessing the proliferation or differentiation behaviour of a population of target cells in a biological system, said method further comprising comparing at least one further parameter predicted or described by application of the Master Equation to said target cell population with at least one further parameter predicted or described by application of the Master Equation to a reference cell population, and identifying parameters which are altered in said target cell population, thereby characterising the changes in the proliferation or differentiation behaviour of the target cells.

Preferably comparisons made to parameters determined with reference to the master equation are made to parameters predicted or described by said equation, preferably predicted by said equation.

Labelling

The target cells may be labelled so as to distinguish them from other cells in the population. Preferably, only a small proportion of cells in a population are labelled e.g. fewer than 1 in 27 cells, to allow individual cells and clonal lines descended therefrom to be distinguished within a population, for example within a tissue such as epidermis.

The at least one proliferation characteristic of the target cells may be measured at one or more time points following said labelling.

In some embodiments interventional marking of the cell(s) may not be required, for example if it is desired to follow a subpopulation of cells which already express a detectable cellular marker such as a cell surface antigen or similar moiety, or alternatively perhaps if it is desired to follow a clone of cells infected with a particular virus, transposon or similar detectable moiety. The requirement is simply that cells originating from a particular cell or cells be able to be detected at later time point(s) so that information about their proliferation and/or differentiation can be collected according to the present invention.

In some embodiments, cells may be labelled by the expression of a marker gene, for example a gene which encodes a light generating protein, such as green fluorescent protein (GFP), enhanced yellow fluorescent protein or luciferase. Expression of a marker gene may be inheritably activated prior to measurement of the proliferation characteristic.

Inheritable activation is activation which is inherited by the descendent cells produced by cell division from the parent cell in which the original activation was induced i.e. expression of the marker gene is passed from parent cell to daughter cells during cell division, following induction of activation.

In some preferred embodiments, the marker gene may be inheritably activated in a small proportion of cells in the population as described above. This allows individual clonal lines to be distinguished in the population and allows the proliferation characteristics of one, or preferably more than one, clonal line to be measured within the population, for example in tissue from a single test animal.

For example, the value of at least one proliferation characteristic may be measured by
(i) providing a test animal comprising a marker gene,
(ii) inducing inheritable activation of said marker in at least one target cell of said test animal, wherein inheritable activation is induced in fewer than 1 in 27 cells in the tissue, for example epidermis,
(iii) incubating the test animal,
(iv) visualising those clonal cells which express the marker gene as a result of the inheritable activation, and
(v) measuring the value of the at least one proliferation characteristic in the visualised clonal cells.

Preferably, inheritable activation of the marker gene is induced at a level that leads to inheritable activation in fewer than 1 in 27 cells, preferably fewer than 1 in 30 cells, preferably fewer than 1 in 40 cells, preferably fewer than 1 in 60 cells, preferably fewer than 1 in 100 cells, preferably fewer than 1 in 150 cells, preferably fewer than 1 in 200 cells, preferably fewer than 1 in 300 cells, preferably fewer than 1 in 400 cells, preferably fewer than 1 in 500 cells, preferably fewer than 1 in 600 cells, preferably fewer than 1 in 635 cells, preferably fewer than 1 in 653 cells, preferably fewer than 1 in 700 cells, preferably fewer than 1 in 800 cells, preferably fewer than 1 in 900 cells, preferably fewer than 1 in 1000 cells, or even fewer.

This maximises the probability of the cells expressing the marker gene being spatially separated and thereby facilitates visualisation. The optimum rates of recombination will vary from tissue to tissue depending upon the cellular makeup and cell spacing which varies from tissue to tissue.

The genetic construct such as the marker gene may be directed into a particular locus of the test animal's genome, preferably an ubiquitously expressed locus such as the hprt or Rosa locus, preferably the Rosa locus. The expression of a gene of interest such as an oncogene contained in the construct may be restricted by using a tissue specific promoter, such as keratin 5 which directs expression to the basal layer of the epidermis.

Inheritable activation may be induced by inducing recombination in the at least one cell which produces expression of said marker gene.

This may be achieved using a heritable somatic recombination system which is tightly regulated so that no background recombination events, or no significant background recombination events, are observed. Recombination induction may occur at a sufficiently low frequency that on average individual recombination events occur in cells which are sufficiently spatially separated to allow the daughter cells from each of the individual cells to be followed without the physical expansion of the clones causing a merging or demerging of the individual marked populations.

Suitable recombination systems include the cre-lox recombinase or flp recombinase systems. An inducible flp system may be used. In particular, the cre-lox system is preferred, preferably an inducible cre-lox system. Particularly preferred is the AhcreER$^T$ system (Kemp et al. 2004 NAR vol 32 No. 11). Recombination may be induced and the marker activated in the AhcreER$^T$ mouse by the administration of B-napthoflavone and tamoxifen.

The test animal may comprise one or more preferably more than one individually labelled clonal cell lines. By incubating the animal, the individual clonal lines are also being incubated i.e. the clonal lines are incubated in vivo in the tissue of the mouse in which they were generated. However, clearly the incubation overall (i.e. the animal) takes place in vitro in a suitable laboratory setting.

Incubation allows the normal processes for cell division, migration or differentiation to take place. Thus, test animals are given their normal levels of care and their normal diet and as far as possible normal conditions during the incubation stage. The cells may then expand (or not expand) as they normally would in the particular micro-environment in which they find themselves within the test animal. This is allows the biologically relevant in vivo processes to be investigated.

Visualisation may be by any suitable means. For example, a marker may be used which is later detected by an antibody which mediates the visualisation. Alternatively, the marker may itself be light emitting, for example fluorescent. Most preferred are markers which are themselves fluorescent, such as enhanced yellow fluorescent protein.

Other visualization means include fluorescent proteins, proteins expressing an epitope tag, allowing visualisation with anti-tag immunoflourescence, proteins which are themselves immunogenic and can be visualised by immunoflourescence, e.g. mutant p53.

Fluorescent and/or tagged proteins can be expressed from the same RNA as the gene of interest by using an IRES sequence or as a fusion protein with the gene of interest. Alternatively, fluorescent and/or tagged proteins can be included in a loxP flanked STOP cassette, so that clones are identified by loss of the fluorescent or tagged protein. Advantageously these complementary approaches can be combined e.g. by including a blue fluorescent protein in the STOP cassette, and a yellow fluorescent protein expressed from an IRES with the gene of interest. In this embodiment, following recombination the cells would convert from blue to yellow.

The target cell and clonal cells descended therefrom may be visualised, for example, by confocal microscopy, preferably wholemount confocal microscopy (Braun et al. 2003 Development 130 5241-5255).

The methods described herein may be useful in determining the effect of a test compound on cell growth behaviour, for example cell proliferation and/or differentiation, for example in toxicity or carcinogenicity studies or in screening for anti-proliferative agents for use in therapy or cosmetics. For example, target cells as described herein may be treated with a test compound before the at least one proliferation characteristic is measured, and the effect on cell proliferation determined. Changes in the proliferation and/or differentiation of the treated target cells relative to controls may be indicative that the test compound alters or affects cellular proliferation. Changes may, for example, be indicative that the test compound is toxic or carcinogenic or may be indicative of beneficial cosmetic properties.

In embodiments in which the target cells are within the tissue of a test animal, the cells may be treated with test compound by administering the test compound to a test animal which comprises the target cells e.g. by injection or by other means of systemic introduction into the test animal such as oral administration, or by topical application e.g. by 'painting' or otherwise locally administering the substance or composition. In some preferred embodiments, the target cells are within the epidermis of a test animal and the test compound is applied topically to the epidermis. For example, the test animal may be a mouse and administration may be by topical application to the tail skin, preferably to the exterior of said skin. A tissue sample may be removed from the animal to in order to measure the value of at least one proliferation characteristic of the treated target cells at one or more time points following application of the test compound.

Many individual physically separated cell clones can be created in the epidermis of a single test animal and the value of one or more proliferation characteristics measured separately for each individual clone.

A method of assessing the effect of a test compound on cell growth behaviour may comprise:

(a) treating target cells in a population with a test composition or substance, (b) measuring the value of at least one proliferation characteristic of said treated target cells;

(c) comparing the measured value with the value predicted for said characteristic for normal mammalian cells in the population by a model of cell growth behaviour, wherein said model of cell growth behaviour requires a parent cycling cell to divide into either 1) two cycling daughter cells, 2) a cycling and a non-cycling daughter cell or 3) two non-cycling daughter cells; and none of the cells in said population is a stem cell, (d) determining the likelihood of changes in the growth behaviour, for example the proliferation and/or differentiation, of said treated target cells from the difference in said measured and predicted values, wherein an increased likelihood of changes in the presence relative to the absence of test compound is indicative that the test compound affects cell growth behaviour.

Target cells within the epidermis of a test animal, for example a rodent such as a mouse, may be treated with a test compound, for example a candidate cosmetic, by topical administration of the compound to the skin of the animal.

Samples of epidermal tissue may be obtained and analysed following the administration to measure the proliferation characteristic of the target cells.

A suitable test animal may comprise an inheritably activatable marker gene, whose activation can be induced in fewer than 1 in 27 cells in the epidermal tissue, as described above.

Methods described herein are useful in screening compounds for toxicity or carcinogenicity. A method of assessing the toxicity and/or carcinogenicity of a substance or compound may comprise:

(a) treating target cells in a population with a test compound or substance
(b) measuring the value of at least one proliferation characteristic of said treated target cells;
(c) comparing the measured value with the value predicted for said characteristic for normal mammalian cells in the population by a model of cell growth behaviour,
   wherein said model of cell growth behaviour requires a parent cycling cell to divide into either 1) two cycling daughter cells, 2) a cycling and a non-cycling daughter cell or 3) two non-cycling daughter cells; and none of the cells in said population is a stem cell,
(d) determining the likelihood of changes in the growth behaviour, for example the proliferation and/or differentiation, of said treated target cells from the difference in said measured and predicted values,
   wherein an increased likelihood of changes in the presence relative to the absence of test compound or substance is indicative that the test compound or substance is toxic and/or carcinogenic.

Suitable substances or compounds may include any potential or candidate carcinogen or toxin and may be any compound to which animals, including humans, may be exposed, for example in therapeutics, cosmetics, manufactured products or the environment.

In addition to screening for toxic or carcinogenic properties, methods described herein may also useful in screening compounds for beneficial cosmetic properties. A method of assessing the cosmetic properties of a substance or compound may comprise:
(a) treating target cells in a population with a test compound or substance
(b) measuring the value of at least one proliferation characteristic of said treated target cells;
(c) comparing the measured value with the value predicted for said characteristic for normal mammalian cells in the population by a model of cell growth behaviour,
   wherein said model of cell growth behaviour requires a parent cycling cell to divide into either 1) two cycling daughter cells, 2) a cycling and a non-cycling daughter cell or 3) two non-cycling daughter cells; and none of the cells in said population is a stem cell,
(d) determining the likelihood of changes in the growth behaviour, for example the proliferation and/or differentiation, of said treated target cells from the difference in said measured and predicted values,
   wherein an increased likelihood of changes in the presence relative to the absence of test compound or substance is indicative that the test compound or substance may have beneficial cosmetic properties.

Beneficial cosmetic properties may include the inhibition or reduction of cell proliferation and/or differentiation. A test compound or substance identified using the present methods as inhibiting or reducing cell proliferation and/or differentiation may be useful as a cosmetic agent.

The values of the parameters in the cell growth behaviour model which describe the proliferation and differentiation of the treated target cells may be determined in the methods described herein. A method may comprise producing a model which describes the proliferation and differentiation of the treated target cells by fitting the cell growth behaviour model described above to the measured value of the at least one proliferation characteristic of the treated target cells by adjusting the parameters and/or assumptions which are used to characterise the proliferation and differentiation of the untreated target cells, thereby obtaining a cell growth behaviour model with adjusted parameters and/or assumptions which describes the proliferation and differentiation of the treated target cells.

The parameters of the model which describes the proliferation and differentiation of the treated target cells may be compared with the parameters of the model which describes the proliferation and differentiation of the untreated target cells and the parameters which are altered by treatment with the test compound identified.

As described above, the target cells may be within the tissue of a test animal, such as the epidermis.

In some preferred embodiments, the target cells do not contain active p53 i.e. p53 has been inactivated or suppressed in the target cells. Suitable methods for inactivating or suppressing p53 are well known in the art.

The methods described herein may also be useful in screening for compounds which restore normal growth behaviour on target cells which are have altered, for example abnormal growth behaviour. Target cells with abnormal growth behaviour may include cells with excessive proliferation, such as cancer cells or cells expressing an oncogene.

A method may, for example, comprise treating target cells which have altered or abnormal growth behaviour, for example altered or abnormal proliferation and/or differentiation, with a test compound, and then measuring the at least one proliferation characteristic of the target cells as described above.

The effect of the test compound may be determined on the basis of the difference between the measured value of the proliferation characteristic in the treated target cells and the value predicted for that proliferation characteristic in untreated cells by the model.

For example, the likelihood that the altered growth behaviour in the treated target cells is reduced or abrogated or that normal growth behaviour is increased or promoted may be determined from the difference in said measured and predicted values. A reduced likelihood of altered growth behaviour or increased likelihood of normal growth behaviour in cells treated with the test compound may be indicative that the test compound is an anti-proliferative agent, which may be useful as a cancer therapeutic or cosmetic.

The test compound may be a candidate carcinogen or toxin. In this embodiment, changes in the growth behaviour of the treated target cells relative to controls are indicative that the test compound is a carcinogen or toxin.

The test compound may be a candidate cosmetic agent. In this embodiment, changes in the growth behaviour of the treated target cells relative to controls are indicative that the test compound is a candidate cosmetic agent.

As described above, the values of the parameters in the cell growth behaviour model which describe the proliferation and/or differentiation of the treated target cells may be determined. A method may comprise producing a model which describes the proliferation and differentiation of the treated target cells by fitting the cell growth behaviour model described above to the measured value of the at least one proliferation characteristic of the treated target cells by adjusting the parameters and/or assumptions which are used to characterise the growth behaviour of the untreated target cells, thereby obtaining a cell growth behaviour model with adjusted parameters and/or assumptions which describes the proliferation and differentiation of the treated target cells. The parameters of the model which describes the proliferation and differentiation of the treated target cells may be compared with the parameters of the model which describes the proliferation and differentiation of the untreated target cells and the parameters which are altered by treatment with the test compound identified.

Target cells which have altered growth behaviour which are suitable for use in the methods described above include cells expressing an oncogene or other gene which alters cell proliferation. A method may, for example, comprise expressing a gene which alters cell proliferation and/or differentiation in the target cells, for example an oncogene such as Gli-1 and treating the target cells expressing the gene with the test compound, before measuring the at least one proliferation characteristic as described above.

A reduction or abrogation in altered proliferation and/or differentiation in the treated cells relative to controls (i.e. untreated cells) is indicative that the test compound can restore normal proliferation and/or differentiation on cells which are proliferating abnormally and may be useful in the treatment of cancer.

Furthermore, the expression of the gene which alters cell proliferation and/or differentiation may be restricted by using a tissue specific promoter, such as keratin 5 which directs expression to the basal layer of the epidermis.

The methods described herein may also be useful in determining the effect of genes on cell proliferation and/or differentiation. This may be useful, for example in the identification of oncogenes. A method may comprise expressing a test gene in the target cells and then measuring the at least one proliferation characteristic of the target cells as described above.

The effect of the test gene may be determined on the basis of the difference between the measured value of the proliferation characteristic in the target cells expressing the test gene and the value predicted for that proliferation characteristic by the cell growth behaviour model in target cells not expressing the test gene (e.g. cells undergoing normal proliferation and differentiation).

For example, the likelihood that the expression of the test gene alters cell proliferation and/or differentiation may be determined from the difference in said measured and predicted values. An increased likelihood of altered proliferation and/or differentiation in cells expressing the test gene may be indicative that the test gene is an oncogene or other gene which alters cell proliferation and/or differentiation.

As described above, the values of the parameters in the cell growth behaviour model which describe the proliferation and/or differentiation of the target cells expressing the test gene may be determined. A method may comprise producing a model which describes the proliferation and differentiation of the target cells expressing the test gene by fitting the cell growth behaviour model described above to the measured value of the at least one proliferation characteristic of the target cells expressing the test gene by adjusting the parameters and/or assumptions which are used to characterise the proliferation and differentiation of the target cells in the absence of expression of the test gene, thereby obtaining a cell growth behaviour model with adjusted parameters and/or assumptions which describes the proliferation and differentiation of the target cells expressing the test gene. The parameters of the model which describes the proliferation and differentiation of the target cells expressing the test gene may be compared with the parameters of the model which describes the proliferation and differentiation of target cells not expressing the test gene and the parameters which are altered by expression of the test gene identified.

The test gene may be a candidate oncogene, cell cycle regulator, a gene controlling asymmetric cell division or terminal differentiation, regulating a cell signalling pathway or cell-cell adhesion or other gene suspected of affecting cell proliferation and/or differentiation.

Another aspect of the invention provides a computer program product carrying such computer-readable code which allows a processor programmed therewith to:

a) predict the value of a proliferation characteristic for normal cells in the population using a model of cell growth behaviour as described above,
   wherein said model of cell growth behaviour requires a parent cycling cell to divide into either 1) two cycling daughter cells, 2) a cycling and a non-cycling daughter cell or 3) two non-cycling daughter cells; and none of the cells in said population is a stem cell, b) compare the value of said proliferation characteristic which is measured in target cells with said predicted value for normal cells, and, c) determine the likelihood of altered cell growth behaviour of said target cells, for example altered proliferation or differentiation, from the difference in said measured and predicted values.

The computer-readable code may further allow the processor programmed therewith to fit the cell growth behaviour model to data from normal cell proliferation and differentiation, for example one or more measured values for proliferation characteristics of normal cells, to predict the value of the proliferation characteristic for normal cells.

The computer-readable code may further allow the processor programmed therewith to determine values of the parameters in the cell growth behaviour model which describe the altered proliferation and/or differentiation of the target cells. For example, the processor may fit the cell growth behaviour model as described above to the measured value of the at least one proliferation characteristic of the target cells by adjusting the parameters and/or assumptions which are used to characterise normal cell proliferation and differentiation, thereby obtaining a cell growth behaviour model with adjusted parameters and/or assumptions which describes the altered proliferation and/or differentiation.

The processor so programmed may compare the parameters of the model describing altered proliferation and/or differentiation with the parameters of the model describing normal proliferation and differentiation and thereby identify the amount or extent of alteration of the parameters in the altered model. This allows the changes in the proliferation and/or differentiation to be characterised.

Thus, the invention provides a computer program product carrying such computer-readable code which allows a processor programmed therewith to perform a method as described herein. Clearly, the measuring steps may be carried out by a computer separate from the computer used to carry out the analytical steps, or said measuring steps may be carried out by a technician. Therefore, preferably the computer program product carries such computer-readable code which allows a processor programmed therewith to perform the non-measuring steps of a method described herein, i.e. those steps other than the measurement of the proliferation characteristic(s) (e.g. clone sizes).

As described above, the target cells may be treated with a test compound and the probability that the test substance alters proliferation and/or differentiation and is, for example, a candidate cosmetic or a candidate carcinogen or toxin, determined on the basis of the measured proliferation characteristic.

Further aspects of the invention provide: (i) computer-readable code for programming a processor to assess changes in the cell growth behaviour, for example the proliferation and/or differentiation, of target cells in a population for example as described above, (ii) a computer program product carrying such computer-readable code, and (iii) a computer system configured to assess changes in the growth behaviour, for example the proliferation and/or differentiation, of target cells in a population, from the measurement of a proliferation characteristic of said cells, as described above.

The term "computer program product" includes any computer readable medium or media that can be read and accessed directly by a computer. Typical media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

Compound Testing

The present invention enables improvements in applications such as predictive drug testing. For example, it is possible to accelerate the rate of cell division in the model system, whilst the underlying mathematical model describing the cell behaviour still holds. Therefore, by accelerating the rate of cell division in the system, but knowing that the system is still constrained to the model described herein, the effect of various compounds or treatments on cell behaviour can be investigated across an advantageously short time frame. One example of this application is to use a retinoid treatment. For example, using mouse tail epidermis as the biological system, the mice can be given approximately two weeks of retinoid treatment such as ATRA treatment. The clone sizes are measured as taught herein. These values are then analysed using the model presented herein. Predictions are made about the cell proliferation behaviour at approximately the twelve week stage. It is surprisingly found that those predictions match the observations. The commercial benefit of this type of application of the invention is that, following the retinoid treatment, the mouse epidermis system at approximately twelve weeks has undergone the equivalent of five years' worth of cell division events. Therefore, using the models of the present invention, predictive compound testing can take place over a dramatically accelerated (i.e. reduced) period of approximately 12-14 weeks, whereas in the prior art this type of study would typically have taken approximately five years. A further advantage of this system is that it vastly decreases the number of test animals such as mice which are needed in order to perform this type of compound testing. This advantage flows from the accelerated time frame, and also flows from the fact that multiple clones per animal can be analysed independently using the techniques described herein.

A further application of the invention is in the field of studying potentially oncogenic genetic mutations. For example, at GLI1 mutant can be introduced into the mice and activated at the same time as the marker (such as EYFP). Over expression of GLI1 is known to promote tumours. Indeed, these tumours are well characterised as basal cell carcinoma tumours. GLI1 is equivalent to hedgehog/patched in humans. By conducting a study in a test animal such as mice involving GLI1 over expression coupled to the marking system for following the clones in which GUI is expressed, it is possible to perform predictive anti-cancer studies. For example, Tazoratine™ (Allergan Inc.) is a GLI1 inhibitor. Using the systems of the present invention, the biologically relevant question of whether inhibition of GLI1 is a useful tool in the prevention or treatment of cancer can be addressed.

This is preferably performed as outlined above, by inducing simultaneous GLI1 over expression and cell marking with enhanced yellow fluorescent protein (EYFP). Control mice can then be left untreated, or treated with vehicle. Test mice can then have Tazoratine™ treatment, or treatment with any other candidate compound which might have a beneficial effect on a cancerous cell growth. The proliferation or differentiation behaviour of the target cells in those mice can then be analysed according to the present invention. This advantageously allows analysis of the effects on cell behaviour/homeostasis in a very short time frame. Furthermore, there are practical and moral advantages to using this system such as the significant reduction in the number of test animals required. For example, it is possible to perform the same studies with only a quarter of the animals previously required, or even less. In addition, the need to age cohorts of test animals is removed by following the teachings of the present invention, since the early stage observations can be extrapolated using the mathematical techniques set out herein. This allows prediction of cell proliferation and differentiation behaviour at time frames much later in the treatment. Thus, this advantageously means that the test animals do not need to be maintained under treatment conditions for as long as prior art techniques demand, which beneficially reduces suffering or discomfort in those test animals.

Thus, one of the key advantages provided by the present invention is that it is possible to tell from a very short experiment (for example 2-20 weeks in the case of mice as test animals) if the behaviour of clones is indicative of (e.g.) a cancerous phenotype (e.g. whether or not a particular treatment has carcinogenic outcomes). This is in sharp contrast to prior art studies which require long term maintenance of the test animals.

In addition to performing studies with GLI1, clearly other potential oncogenes or tumour suppressor genes may be studied. Preferred examples of these include p53, Ras and others.

A further application of the systems described herein is to follow the cells or clones of interest by removing them from the test animal and cloning them in vitro. One simple way of accomplishing this is simply to take mouse epidermal cells and to incubate them under ordinary conditions for mouse keratinocyte growth, which are well known to those skilled in the art.

Various further aspects and embodiments of the present invention will be apparent to those skilled in the art in view of the present disclosure.

All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described below.

FIG. 1 shows the organisation of the epidermis. Hair follicles contain stem cells located in the bulge (b), with the potential to generate lower hair follicle (lf), sebaceous gland (sg) upper follicle (uf) and interfollicular epidermis (IFE). Inset: shows the presumed organisation of IFE in previous models, comprising stem cells (S), transit amplifying (TA) cells (TA), and post mitotic basal cells, which migrate out of the basal layer as they differentiate (arrows).

FIG. 2 shows the number of labelled clones per unit area in Ahcre$^{ERT}$ R26$^{EYFP/wt}$ mice from 2 days post induction to 50 weeks.

FIG. 3 shows the total number of cells (both basal and suprabasal) per clone in labelled clones from 2 days post induction to 6 weeks. Error bars indicate sem, as determined by In vivo clonal labelling of epidermal progenitor cells FIG. 4 shows the number of basal cells per clone in labelled clones from 2 days post induction to 1 year; the percentage of clones containing the number of cells indicated in the legend is shown, error bars indicate s.e.m.

Figure 8:
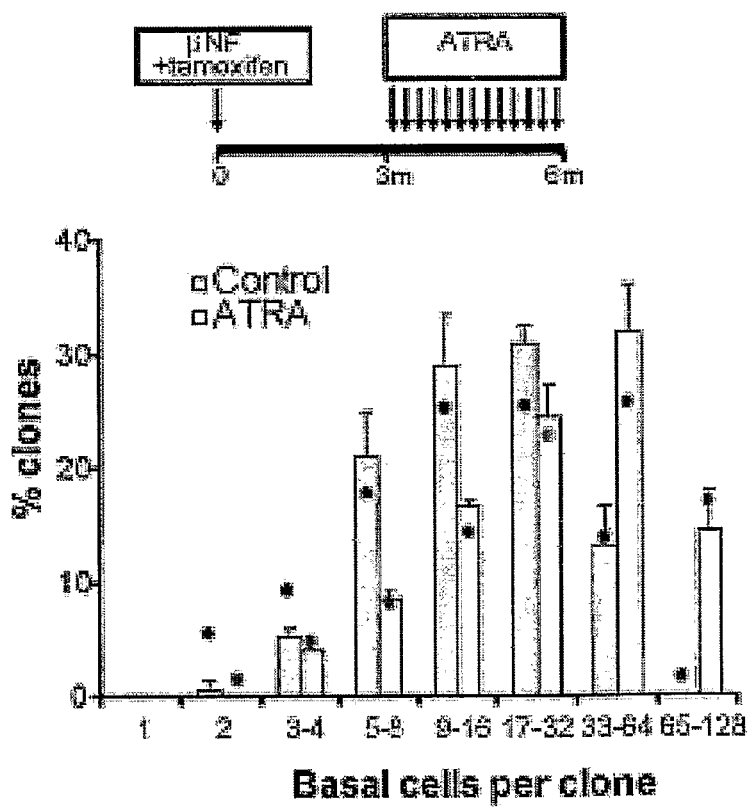

FIG. 8 shows the effects of retinoid treatment. Clone size distribution at 6 months in control and ATRA treated animals were induced and treated following protocol 1; error bars indicate sem. Dark and light points indicate model predictions for control and ATRA treated mice respectively.

Figure 9:
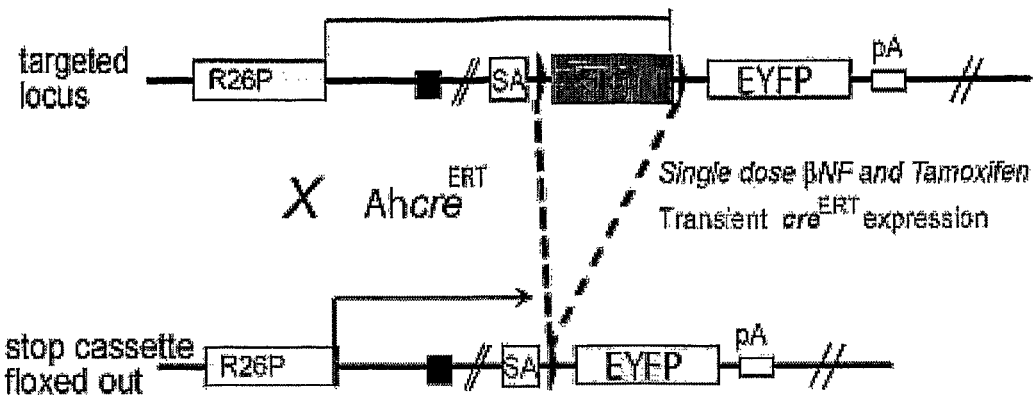

FIG. 9 shows R26EYFP/EYFP mice, with a conditional EYFP (yellow) expression construct containing a "stop" cassette (dark) flanked by LoxP sequences (triangles) targeted to the ubiquitous Rosa 26 promoter, were crossed with the AhcreERT transgenic strain that expresses cre recombinase fused to a mutant oestrogen receptor (creERT) following treatment with βnapthoflavone (βNF) which induces the Ah promoter. In the presence of Tamoxifen, creERT mediates excision of the stop cassette resulting in EYFP expression in the recombinant cell and its progeny.

Figure 10:
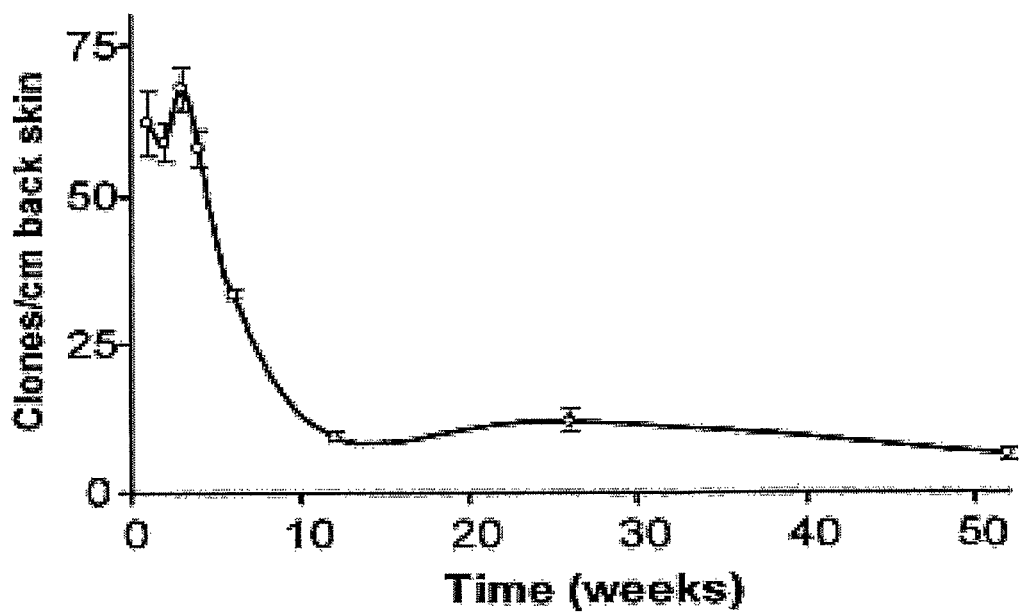

FIG. 10 shows clone density in back skin clones as determined by confocal analysis of cryosections. Clone diameter is expressed as the number of basal cells. Errors bars show sem.

Figure 11:
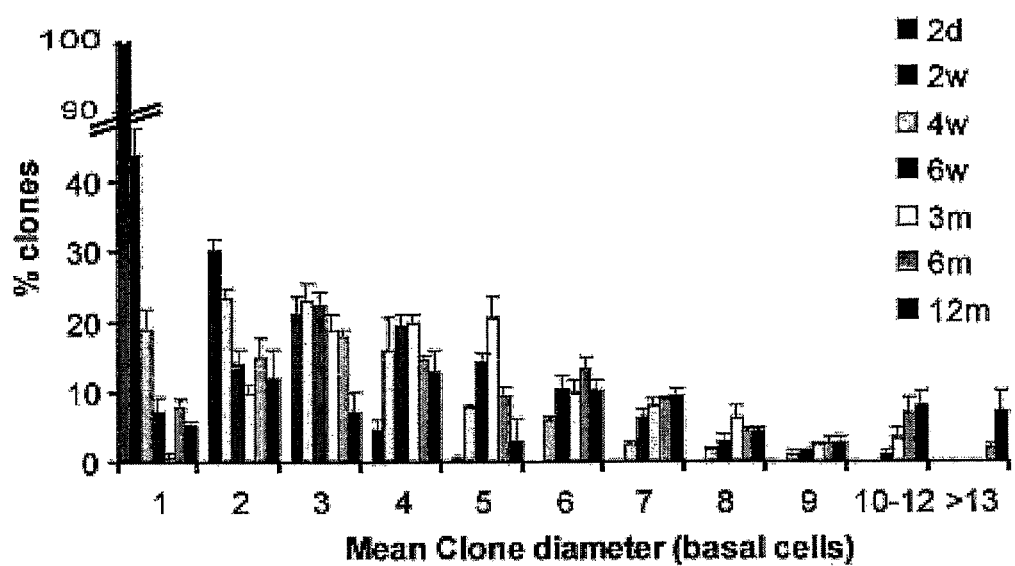

FIG. 11 shows clone size in back skin clones as determined by confocal analysis of cryosections. Clone diameter is expressed as the number of basal cells. Errors bars show sem.

Figure 12:
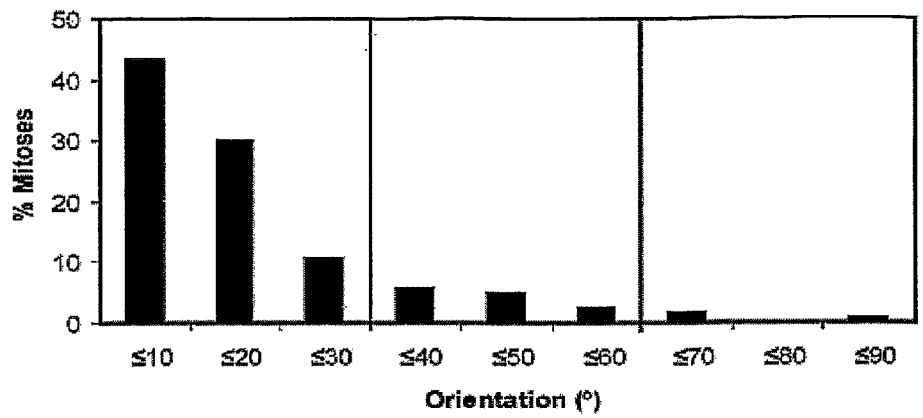

FIG. 12 shows orientation of mitoses to the basal layer in normal epidermis, determined by confocal microscopy of DAPI stained epidermal wholemounts. Left hand panel—planar mitoses, middle panel—oblique mitoses and right hand panel—perpendicular mitoses.

Figure 13:
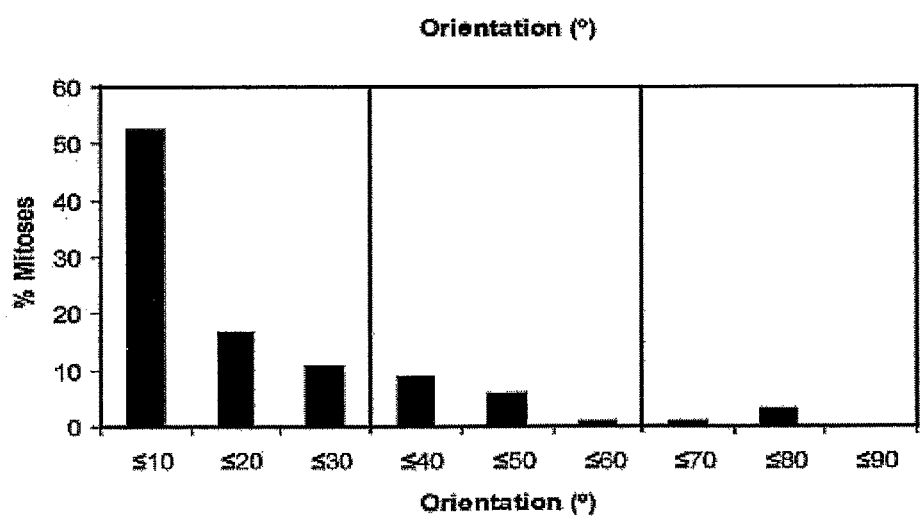

FIG. 13 shows orientation of mitoses to the basal layer after 3 months of ATRA treatment, determined by confocal microscopy of DAPI stained epidermal wholemounts. Left hand panel—planar mitoses, middle panel—oblique mitoses and right hand panel—perpendicular mitoses.

Figure 14:
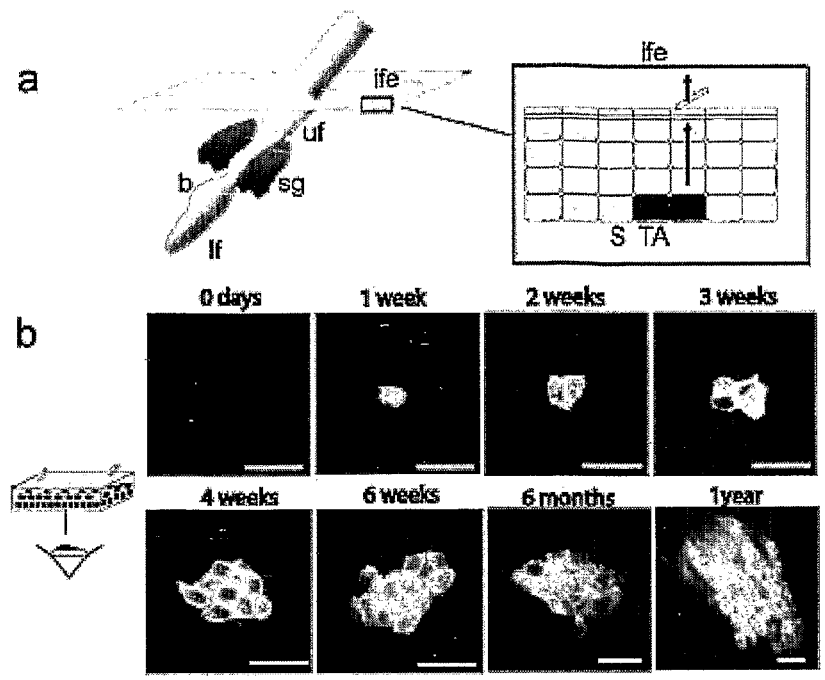

FIG. 14 shows In vivo clonal labelling of epidermal progenitor cells. a, Organization of the epidermis. Hair follicles contain stem cells located in the bulge (b, green), with the potential to generate lower hair follicle (lf), sebaceous gland (sg, orange) upper follicle (uf) and interfollicular epidermis (IFE, beige). The schematic shows the organization of keratinocytes in the IFE (as proposed by the stem/TA cell hypothesis. The basal layer comprises stem cells (S, blue), transit amplifying cells (TA, dark green), and post-mitotic basal cells (red), which migrate out of the basal layer as they differentiate (arrows). b, Projected Z-stack confocal images of IFE wholemounts from Ahcre$^{ERT}$ R26$^{EYFP/wt}$ mice viewed from the basal surface at the times shown following induction. Yellow, EYFP; blue, DAPI nuclear stain. Scale bar, 20 μm.

Figure 15:
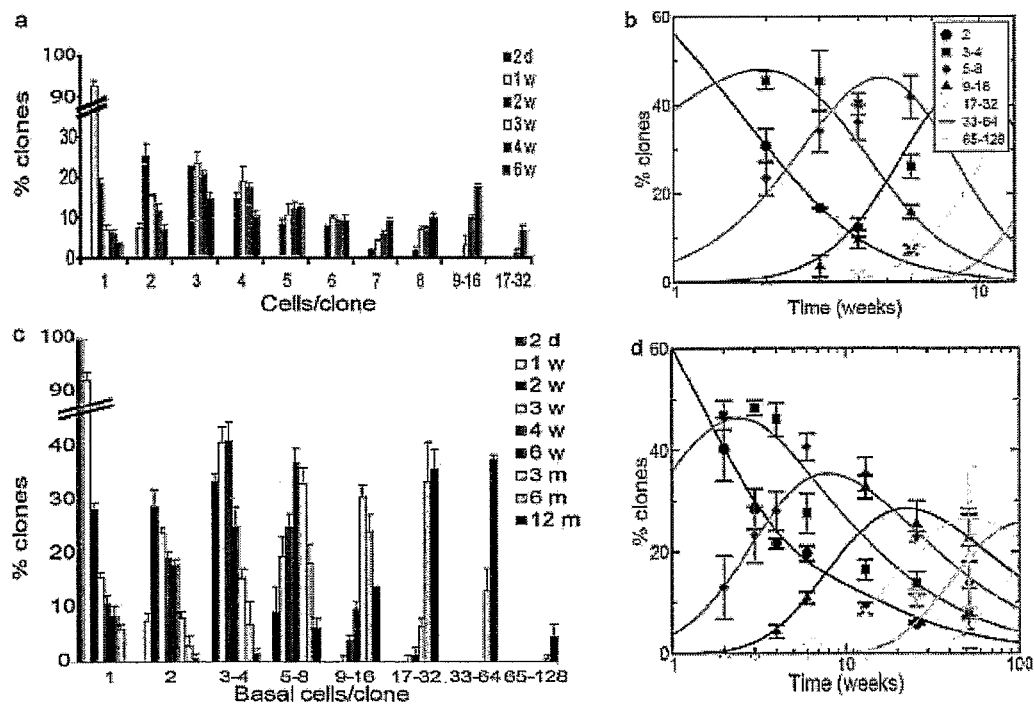

FIG. 15 shows Clone fate data. a, Distribution of clone size (total cells per clone) as a function of cell number, as measured at 2 days, 1, 2, 3, 4 and 6 weeks post-induction (error bars indicate s.e.m.). b, d, Distribution of clone size (total cells per clone) (b) and basal cells per clone (d) as a function of time for different values of cell number (error bars indicate s.e.m.). Here we have aggregated clone sizes in ranges increasing in size in powers of two (see legend within figure). In a preferred embodiment, to advantageously eliminate possible ambiguities due to labelling efficiency, single cell clones are eliminated from the distribution, thereby removing the population of post-mitotic cells labelled at induction. We focus on time points of 2 weeks or more post-induction when EYFP levels have stabilized i.e. after the initial transient period post-labelling. Continuous curves show the behaviour of the proposed one-progenitor-cell model with a cell division rate of λ=1.1 per week and a symmetric division ratio of r=0.08 (see text for details). c, Distribution of basal cells per clone as a function of basal cell number, as measured at 2 days, 1, 2, 3, 4 and 6 weeks, 3, 6 and 12 months post-induction (error bars indicate s.e.m.).

Figure 16:
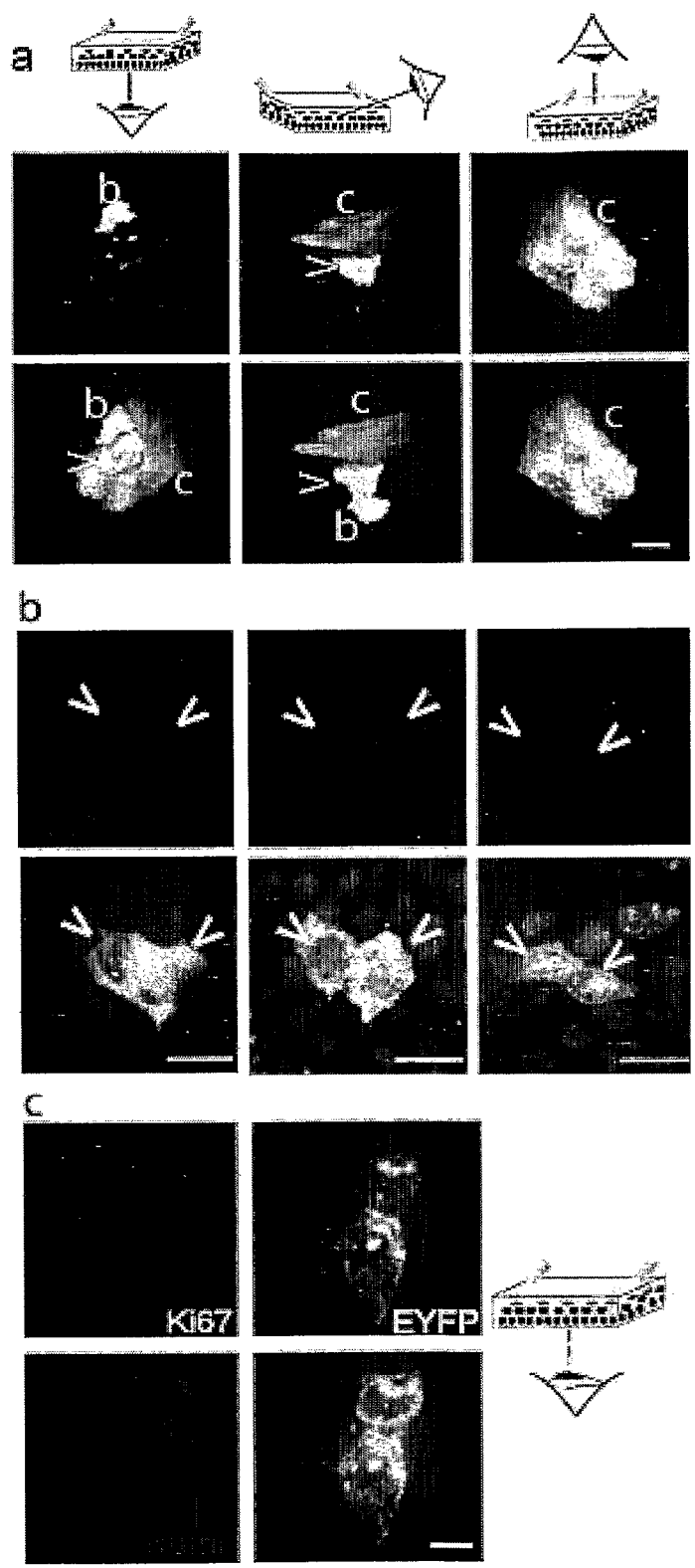

FIG. 16 shows Asymmetric cell fate in epidermal progenitors. a, Visualization of a three-cell clone exhibiting asynchronous terminal differentiation. Projected Z-stack images show one basal cell (b), and two suprabasal cells: a cornified layer cell (c), and a second suprabasal cell indicated by the arrowhead. Cartoon shows the angle of view. Upper panels: EYFP, yellow and DAPI, blue; lower panels are corresponding images with only EYFP shown. Scale bar, 20 μm. b, Visualization of two-cell clones (both cells basal, 3 weeks post-recombination), showing the different proliferative fates of the daughter cells of a single division, providing evidence for symmetric and asymmetric cell fate. Clones are viewed from the basal epidermal surface, stained for the proliferation marker Ki67 (red), DAPI (blue), and EYFP (yellow); arrowheads indicate position of EYFP-labelled cells. Three types of clone are shown, with two, one and zero Ki67 positive cells. Scale bar, 10 μm. c, Two-cell clone (both cells basal, 3 weeks post-recombination, viewed from the basal epidermal surface,) stained for the proliferation marker Ki67 (blue), numb (red) and EYFP (yellow), showing asymmetric distribution of numb, providing evidence for asymmetric cell fate resulting from a planar division. Scale bar, 5 μm.

Figure 17:
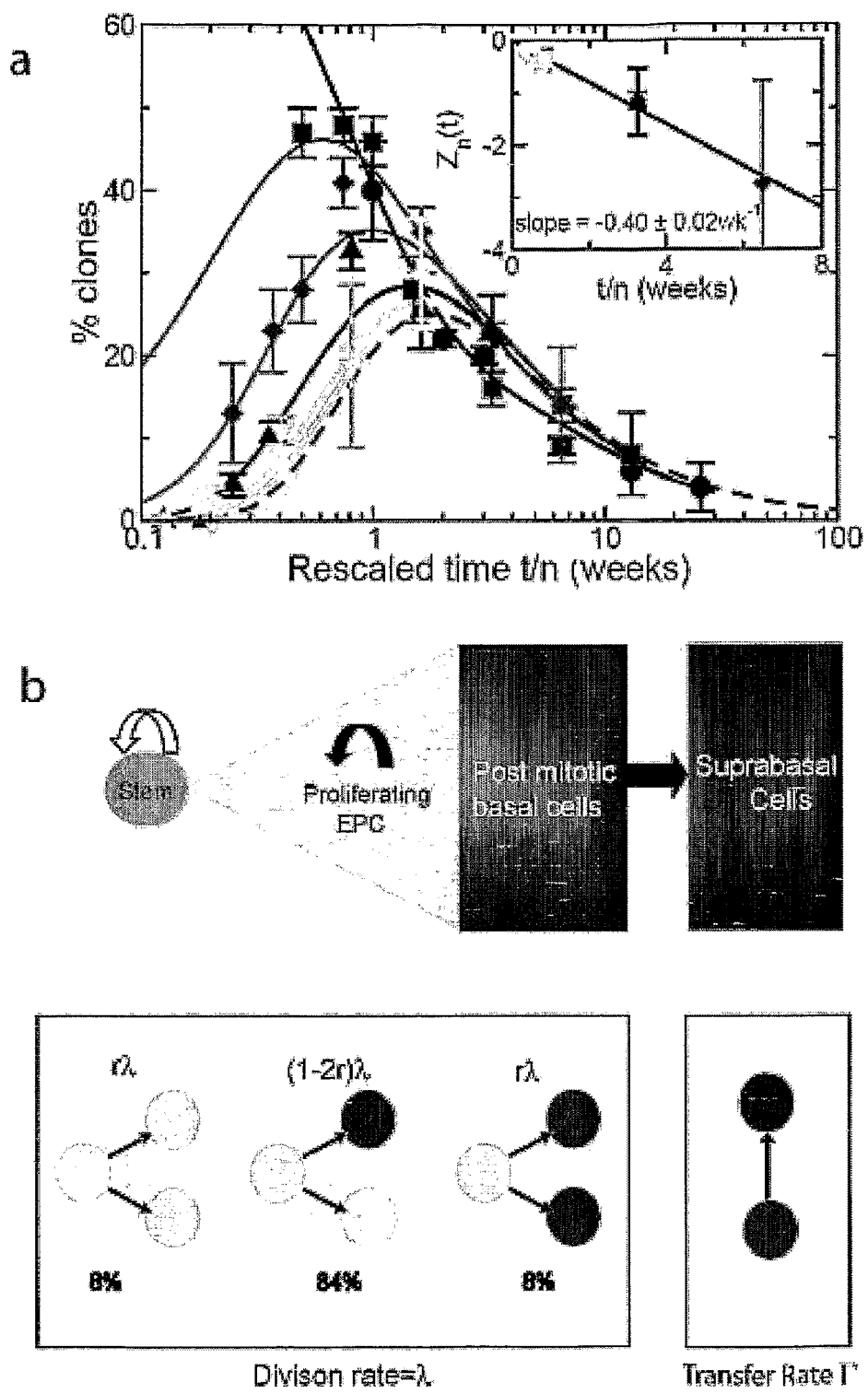

FIG. 17 shows Scaling and model of epidermal progenitor cell fate. a, The basal-layer clone-size distributions (see FIG. 15d legend for key) are replotted against the resealed time coordinate, t/n (where n is taken as the upper limit for each distribution, for example, n=4 for the range 3 to 4, and so on). We note that at long time points (>6 weeks), the data sets for different values of n converge onto a single curve (dashed line); that is, the probability of finding a labelled clone with a basal cell number in the range n/2 to n at time t post-induction is equal to that of finding a clone with a size in the range n to 2n at time 2t. At shorter timescales, the transient behaviour dominates the distribution leading to a departure from simple scaling. This transient behaviour is very well described by the one progenitor cell compartment model (see FIG. 12 caption and main text). Making use of equation (1), we can identify the universal scaling curve for the grouped data as $$G_n(t) \equiv \sum_{m>n/2}^{n} P_m^{pers}(t) = e^{-n\tau/2t} - e^{-n\tau/t},$$

where τ=ρ/rλ; that is, $G_n(t/n)$ is independent of n. Therefore, by plotting $Z_n(t)=1/(2 \ln[(1-(1-G_n(t)^{1/2})/2])$ against t/n (inset) at long times (>13 weeks) and large n (>4), the resulting slope may be used to infer $-1/\tau$. b, The single progenitor compartment model of epidermal homeostasis. A single population of EPCs (green triangle), with unlimited self renewal potential (filled arrow) maintain the epidermis. Post-mitotic cells in the basal layer (light red) transfer at a steady rate to the suprabasal compartment (dark red). The model proposes no role for stem cells (blue) in the steady state, but a quiescent population may play a role in growth in regeneration following injury (unfilled arrow). The left-hand box shows the proliferative characteristics of EPCs. Cycling cells are shown in green, post-mitotic basal cells in light red. The right-hand box shows the transfer of basal post-mitotic cells to the suprabasal layers (dark red). Taken together, these processes with their respective rates summarize the one-compartment model of homeostasis discussed in the text.

Figure 18:
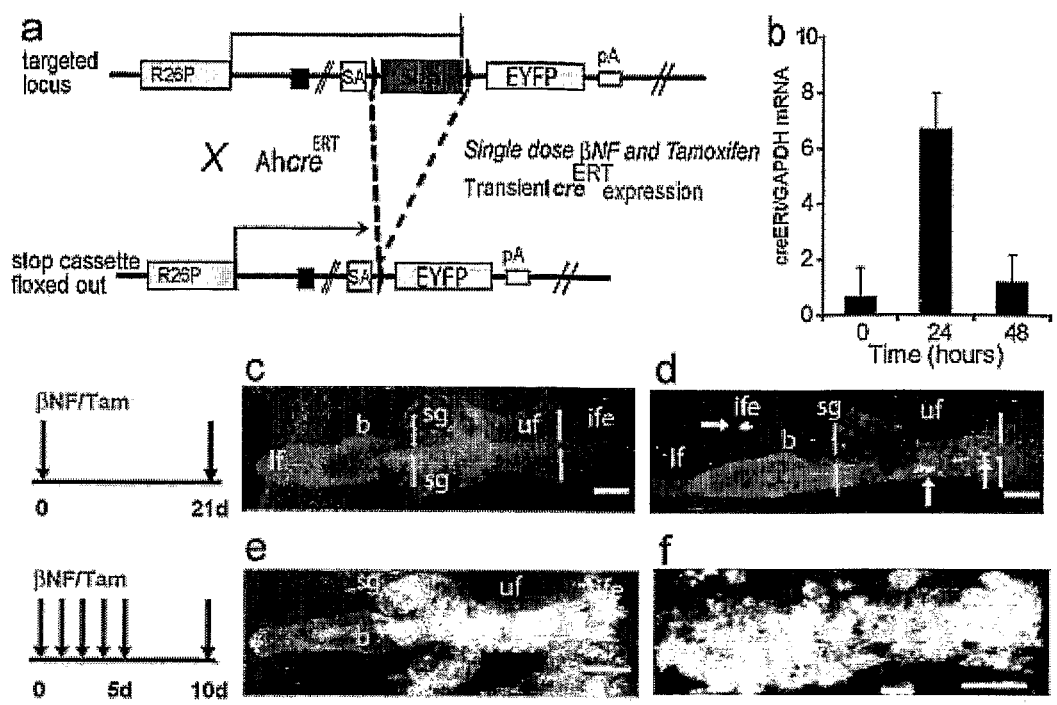

FIG. 18 shows experimental design and promoter characterisation. (a) R26 EYFP/EYFP mice; in presence of tamoxifen creERT mediates excision of stop cassette and EYFP is expressed in the recombinant cell and its progeny. (b) Regulation of creERT in epidermis; after single injection of betaNF; bars are SD. (c)(d)(e) wholemount imaging of tail epidermis, bar is 20 μm.

Figure 19:
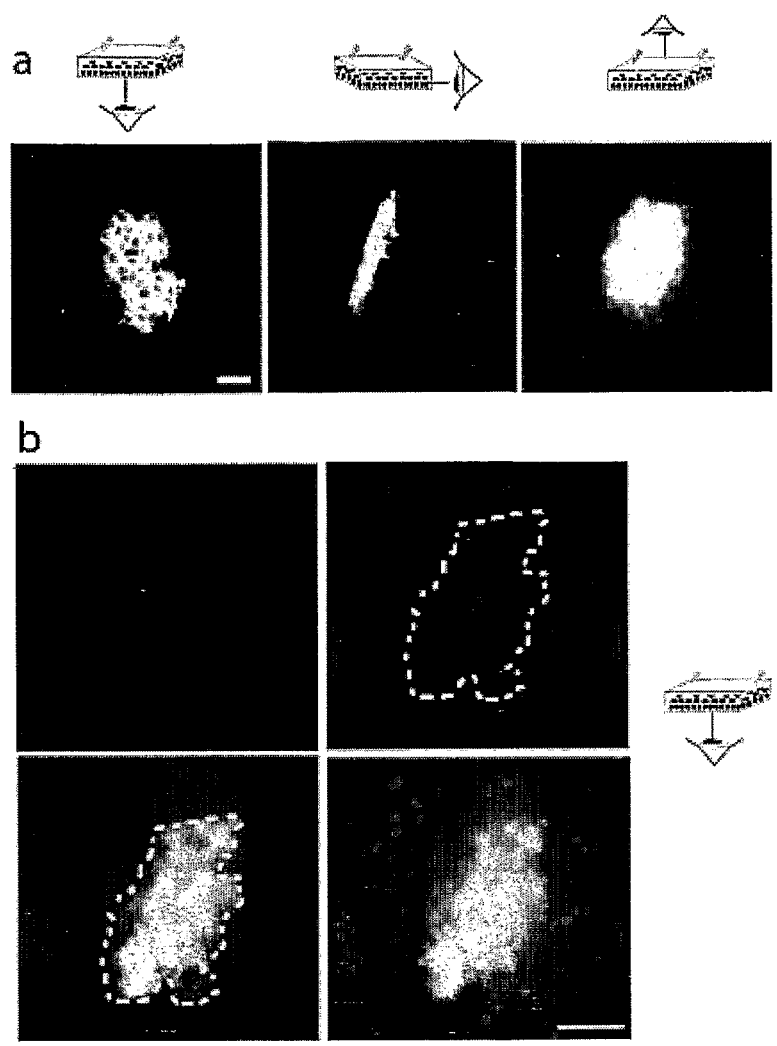

FIG. 19 shows structure of clones at late time points—(a) reconstruction of Z-stack, clone of 6 m, blue DAPI, yellow EYFP, bar 20 μm; (b) clone of 12 m, red Ki67, bar 20 μm.

Figure 20:
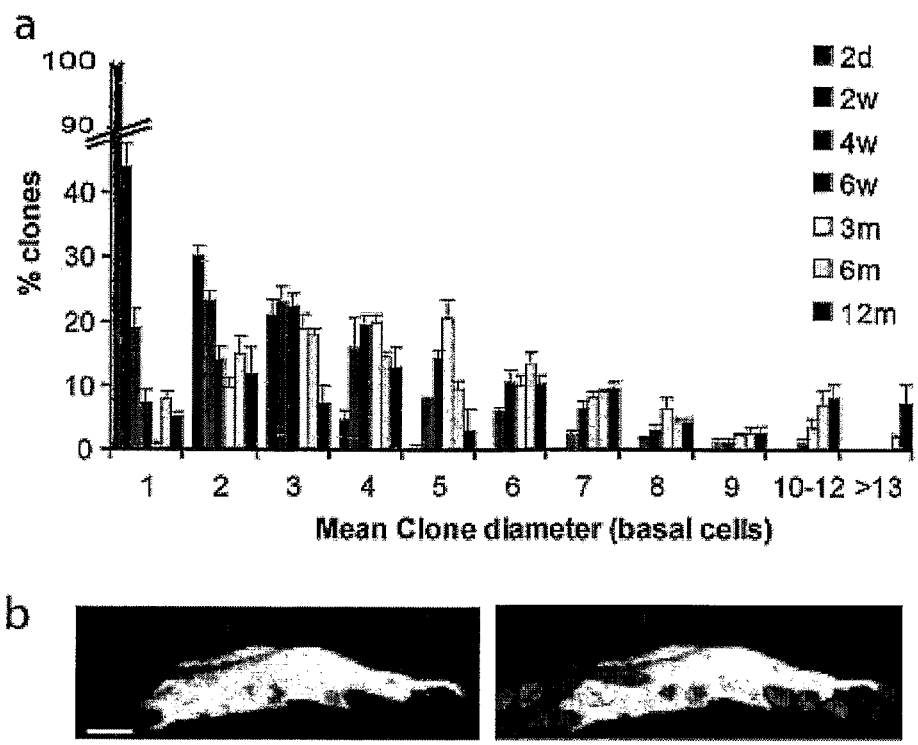

FIG. 20 shows analysis of back skin epidermis; (a) clone diameter by confocal analysis as number of basal cells; bars are SEM; (b) typical clone with dia of 10 basal cells, 1 year post induction; bar 10 μm; yellow EYFP; blue DAPI.

Figure 21:
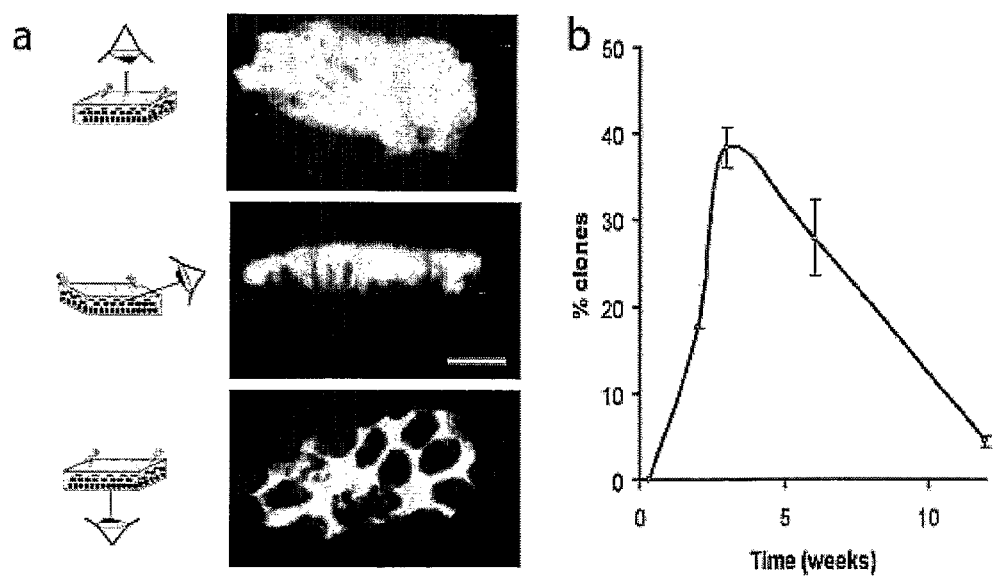

FIG. 21 shows analysis of multicellular clones consisting entirely of suprabasal cells; (a) 2 cell clone; colours as above; bar 10 μm (b) proportion of multicellular clones of only suprabasal cells as a percentage of total number of multicellular clones at given timepoints post induction; bars are SEM.

Figure 22:
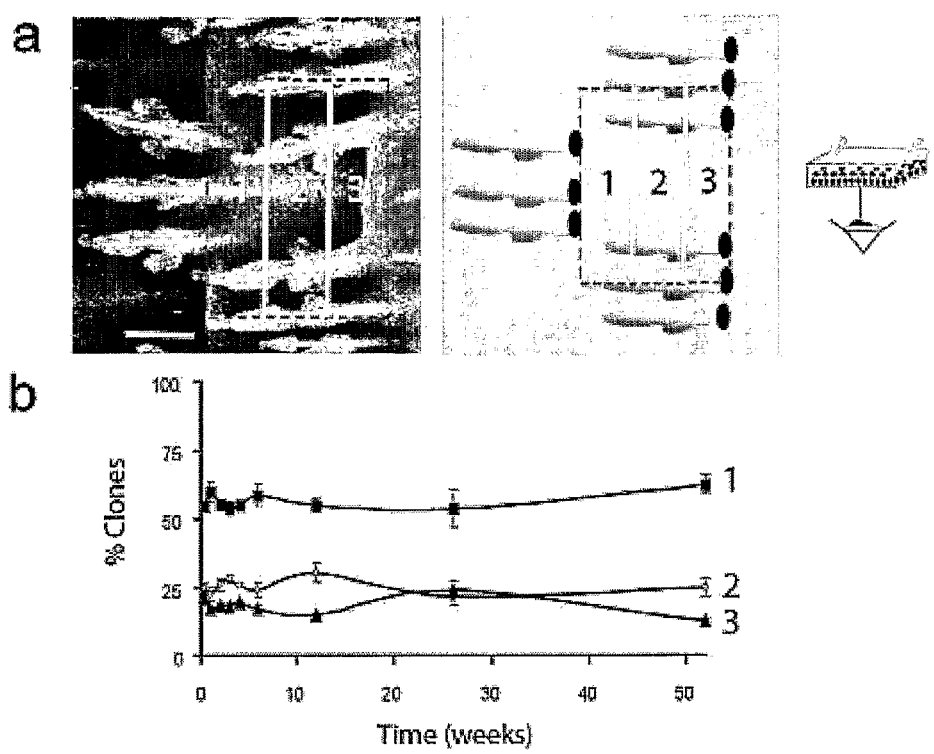

FIG. 22 shows distribution of labelled clones in tail IFE over 1 year following induction; (a) defining a unit area of tail IFE for analysis of clone distribution, bar is 200 um. For analysis of clone distribution each are was divided into 3 regions as shown. (b) mean percentage of labelled IFE clones in 3 regions at each time point; bars are SEM.

Figure 23:
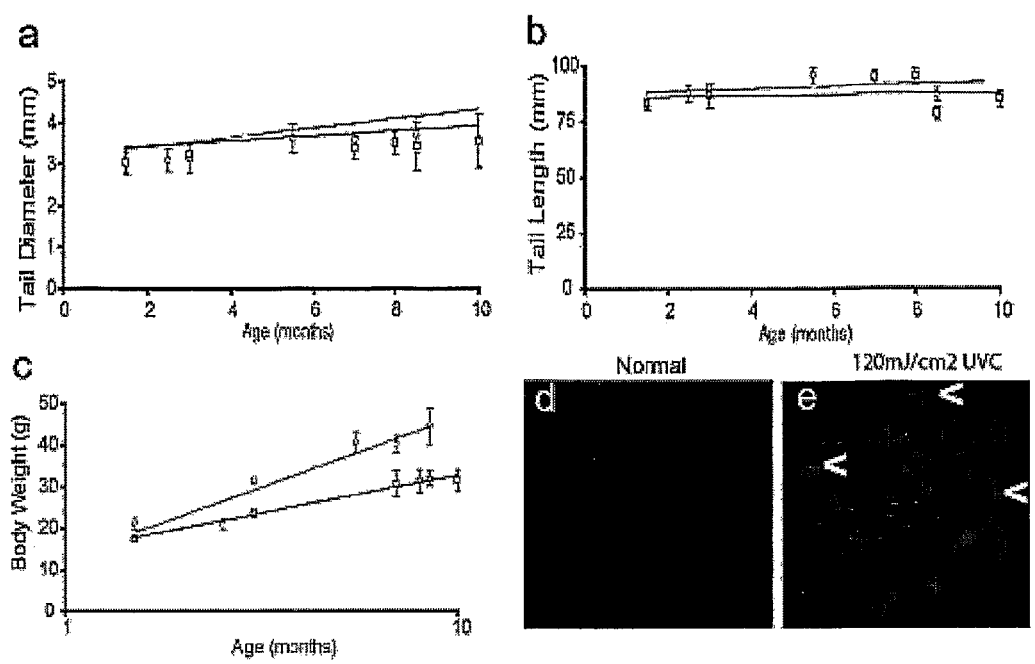

FIG. 23 shows frequency of apoptosis in the basal layer of IFE and also shows Table S1. (a)-(c) epidermal growth (change in tail dia. 2 cm from base of tail); (a) tail length (b) body mass (c) age, bars are SD. (d) and (e); frequency of apoptosis; (d) images of basal layer IFE from 3 w post induction; (e) control; fixed 16 hours after irradiation with 120 mJ/cm2 UVC. Blue DAPI, green cleaved caspase 3; arrows are apoptotic bodies. Table S1 shows frequency of apoptosis by presence of apoptotic bodies or cleaved caspase 3 per basal cell in IFE; 3 w and 6 m post induction.

Figure 24:
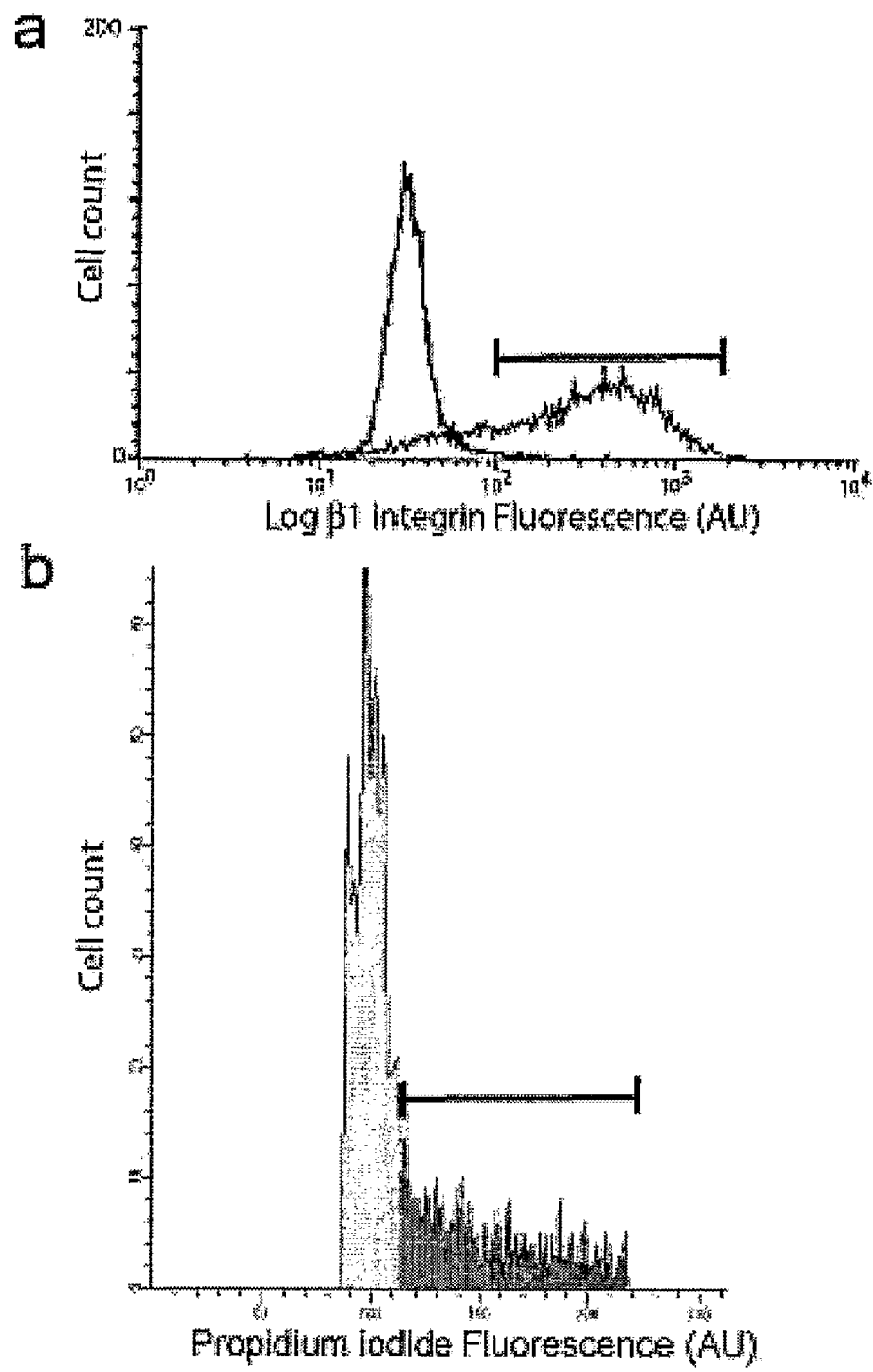

FIG. 24 shows the proportion of cycling cells in IFE; (a) and (b) DNA content of beta 1 integrin positive keratinocytes assessed by flow cytometry; bar is gate for positive cells; (b) shows propidium iodide of beta 1 integrin expressing cells; bar is gate to define cells with >2n DNA (21% in this experiment).

Figure 25:
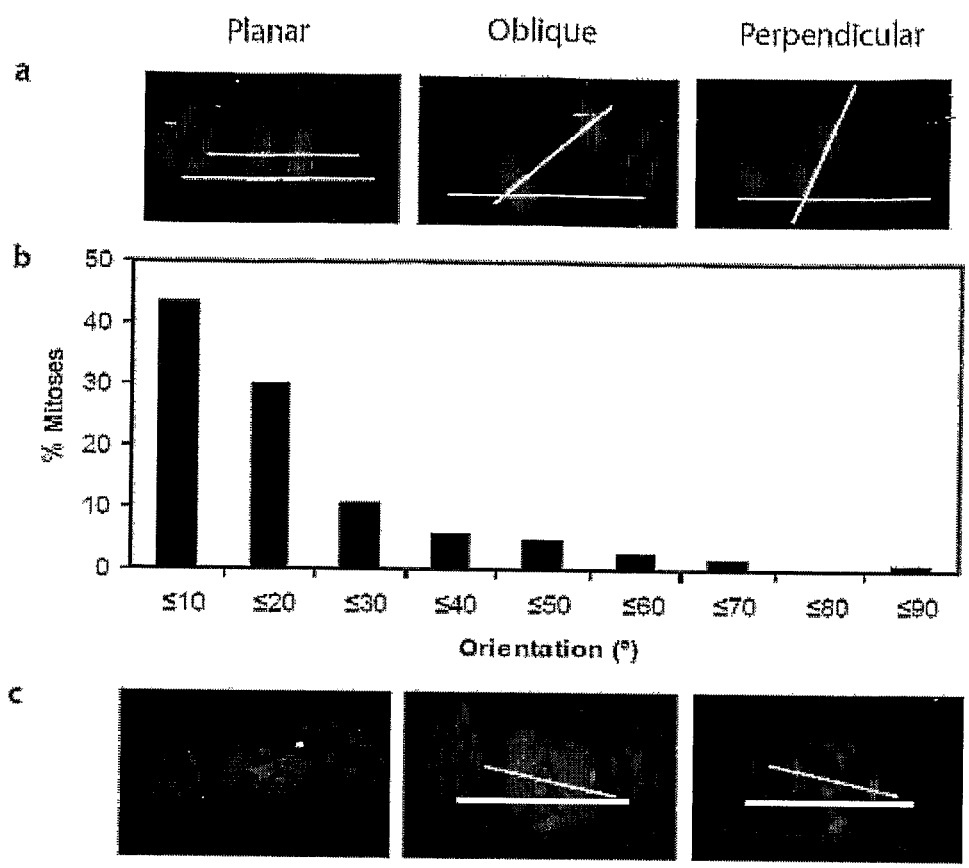

FIG. 25 (a)-(b) shows orientation of mitoses to the basal layer, determined by confocal microscopy of DAPI stained epidermal wholemounts; (c) shows double staining with DAPI (blue) and anti-tubulin (green); orientation assessed by DAPI and tubulin correlated closely; bar is 2 um.

EXAMPLES

Methods

Animals and Sample Preparation

All animal experiments were conducted as specified by Home Office Project License. The generation of AhcreERT and R26EYFP/EYFP mice has been described previously[15, 16]. When AhcreERT R26EYFP/wt mice are treated with multiple doses of βNF and tamoxifen, a high level of recombination was seen in the upper hair follicle and IFE (data not shown). The drug doses were titrated down to produce low frequency labelling; a single intraperitoneal injection of 80 mg/kg β-naphthoflavone (Sigma-Aldrich) and 1 mg tamoxifen free base (MP Biomedicals) dissolved in corn oil resulted in EYFP expression in approximately 1 in 600 basal cells of tail IFE and in 1 in 40 basal cells of back IFE, at two weeks post induction 16. No labelling was detected in the bulge region of the hair follicle and there was no background labelling in untreated AhcreERT R26EYFP/wt animals, even at 15 months of age. Epidermal wholemounts were prepared as described[14]. For analysis of back epidermis, 60 μm cryosections were used.

Immunostaining and Imaging

Immunostaining of wholemounts was performed as described[14]. The following primary antibodies were used; anti GFP conjugated to Alexa Fluor488 or 555 (Molecular Probes), anti Ki67 (Abcam), anti numb (Abcam) and anti cleaved caspase 3 (Cell Signalling Technology). Secondary antibodies were from Molecular Probes. Confocal images are presented as Z-stack projections where 30-120 optical sections in 0.2-2 μm increments, rendered using Improvision Velocity software.

Analysis of Clone Size, Number and Proliferation

Data presented is a typical example of at least 2 experiments with at least 3 mice per time point.

Tail Epidermis

The patterned organisation of tail epidermis, enabled definition of a unit area of tail IFE between adjacent rows of hair follicles which measured 282,000+/−2300 μm2 and contained 4870+/−400 (mean+/−SD) basal layer cells.

The mean number of labelled clones per unit area of tail IFE was assessed by counting all clones detected by confocal imaging of 50 unit areas in each of three mice at each time point, except at 6 and 12 months when 100 areas were counted.

Clone size was determined by Z stack confocal imaging of at least 50 clones containing at least one basal cell in each mouse at each time point. Note that, after 6 weeks anucleate cornified layer cells appear in labelled clones making it impossible to count total cell numbers; hence, the total number of cells per clone was counted up to 6 weeks, but at later time points only basal cells were scored. The percentage of Ki67 positive cells was determined by imaging at least 1500 basal cells in multiple fields from at least 3 mice.

Back Skin Epidermis

60 μm cryosections were analysed by optical sectioning. To determine clone number, all clones in three 10 mm lengths of epidermis were analysed in each mouse at time points up to 3 months; at 6 and 12 month time points at least 5 cm of epidermis was scored for each mouse. The maximum clone diameter, expressed as number of basal cells, was scored for at least 50 clones in each of 3 mice at each time point (FIG. 11).

Apoptosis

Wholemounts of tail epidermis from 2 days, 1 week, 2 weeks, 3 weeks, 4 weeks and 6 weeks after induction were stained with an anti-cleaved caspase3/AlexaFluor488 conjugate; positive Caspase 3 staining was confined to catagen hair follicles.

Analysis of Mitotic Spindle Orientation

Wholemounts of DAPI stained tail IFE were analysed by acquiring Z stacks were of all nuclei containing condensed chromosomes, as revealed by uniform, intense DAPI staining. Images were rendered in 3 dimensions, as above, and spindle orientation of all mitotic figures from metaphase to telophase scored as described[22].

Retinoic Acid Treatment

All trans retinoic acid (Sigma) in ethanol, propanediol 70:30 was applied topically to tail skin and shaved back skin (0.5 ml each) 5 days a week for 3 months at 0.33 mM or daily for 2 weeks at 1 mM.

Example 1

Inducible genetic marking was used to label a sample of cells and their progeny in adult mice. Animals transgenic for the tamoxifen-regulated mutant of cre recombinase (Ahcre$^{ERT}$), expressed from the inducible CYP1A1 promoter, were crossed onto the R26$^{EYFP/EYFP}$ reporter strain, in which a conditional allele of Enhanced Yellow Fluorescent Protein (EYFP) is targeted to the Rosa26 locus (FIG. 8[15,16]). In the resultant Ahcre$^{ERT}$ R26$^{EYFP/wt}$ heterozygotes, EYFP is expressed following a single injection of βNF and tamoxifen at 6-9 weeks of age. At intervals after induction, cohorts of mice were culled for analysis. Cells expressing EYFP and their labelled progeny were detected by confocal microscopy of wholemount epidermis[14].

Figure 1:
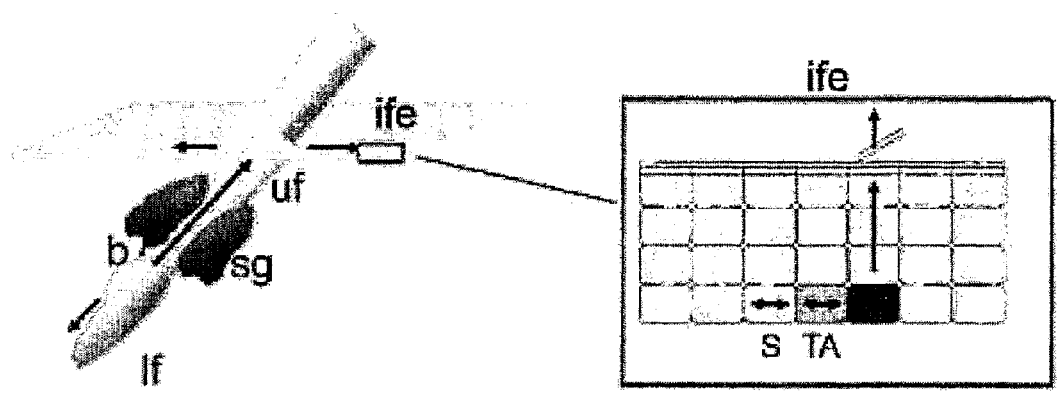
Figure 2:
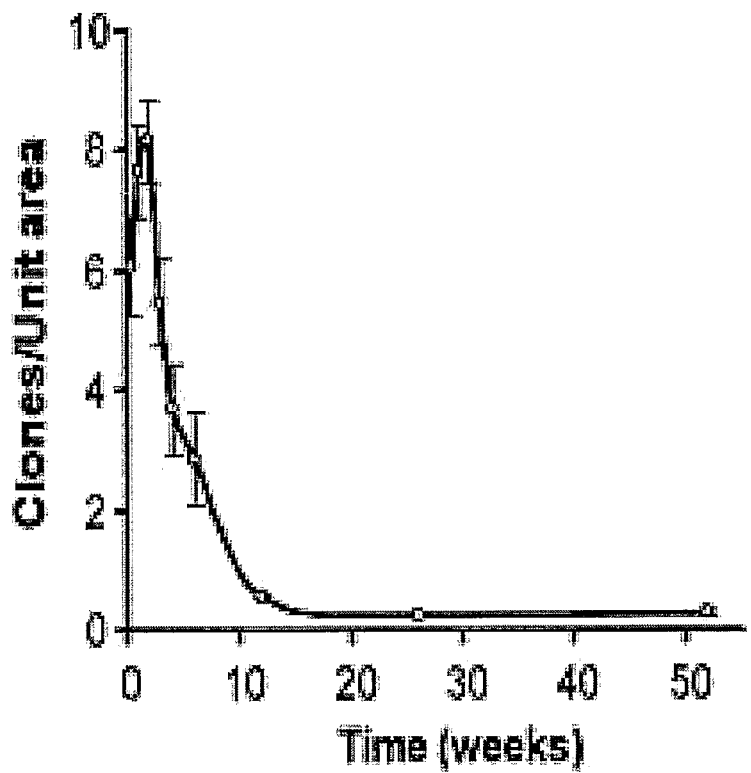

At two days post induction, only single labelled cells were seen in clones in wholemount preparations. Analysis of subsequent cohorts of mice demonstrated clones that remained cohesive and expanded progressively in size. The number of labelled clones per unit area of tail IFE rose as the EYFP label accumulated to a detectable level, peaking at two weeks after induction, and then falling to 6.8% of the peak value by 3 months, and 3.2% at one year; similar results were seen in back skin IFE (FIGS. 2 and 10).

Figure 3:
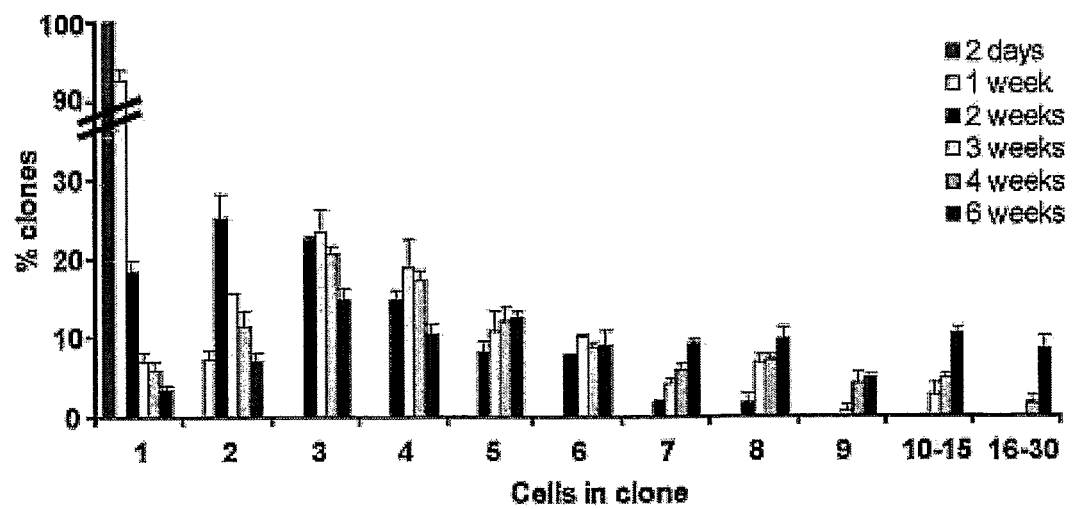

As single cells are labelled at the start of the experiment, and there was no detectable apoptosis in IFE, the total number of cells in each clone provides a direct measure of proliferation since induction. Scoring clones that contained one or more basal cells, we measured the total number of cells per clone up to 6 weeks post labelling, (FIG. 3) and the number of basal cells per clone up to one year. The percentage of proliferating basal cells in tail IFE, assessed by Ki67 immunostaining was found to be 15+/−1% (mean+/−SEM)[17]. Crucially, since there was no significant difference in this figure after one year, and the percentage of cycling basal cells was the same in labelled clones and adjacent unlabelled epidermis, one can infer that (a), over the course of the experiment, the IFE can be considered as a steady-state system, and (b) the cells contained within labelled clones are representative of all EPC. Furthermore, an analysis of the clone distribution in IFE indicates that labelled clones are not replaced by unlabelled clones migrating from hair follicles (FIGS. 12 and 13). As we do not label the bulge of the hair follicle, none of the labelled clones can derive from bulge SC.

All models based on the SC/TA cell hypothesis, including the EPU model, predict that at long-time points the size distribution of the population of SC supported clones must converge to a steady-state, whilst clones which trace their ancestry to a TA or differentiated cell are lost through differentiation. The properties of the TA cell compartment impose an upper limit on number of basal cells in SC supported clones, so that the moments of the clone size distribution (i.e. the average, variance, etc.) must converge to constant values. Such behaviour is in stark contrast to the observed distributions (FIG. 3) which reveal an inexorable increase in clone size. One is therefore driven to consider a different paradigm for the maintenance of the epidermis which does not rely on the SC compartment. We will demonstrate below that the observed behaviour is compatible with a model of homeostasis involving only non stem cells EPC's.

Figure 4:
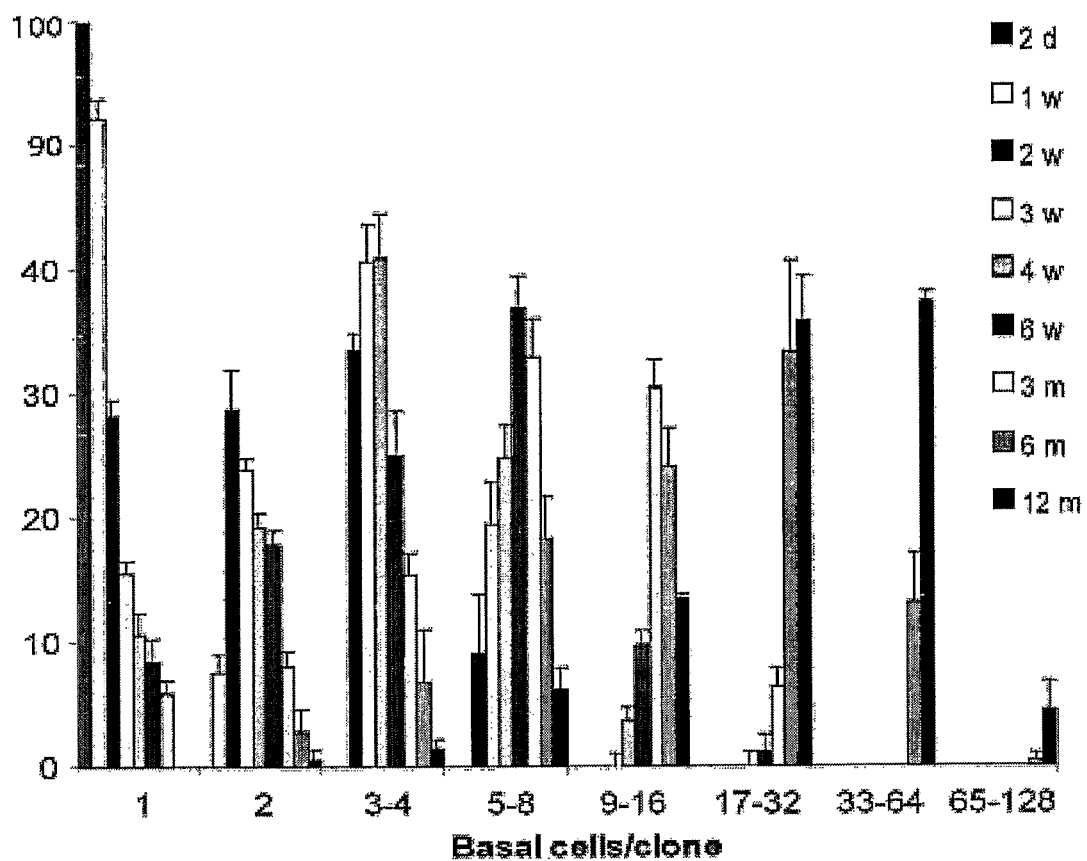

The large body of clonal fate data enabled us to determine the characteristics of the EPC population, using the following additional observations. Firstly, the three-dimensional reconstruction of wholemount epidermis reveals that only 3% of mitotic spindles lie perpendicular to the basal layer, indicating that, in contrast to embryonic epidermis[18,19], the vast majority of EPC divisions generate two basal cells. Secondly, examination of two cell clones at three weeks post induction reveal that cell divisions may generate either one cycling (Ki67 positive) and one non-cycling cell, or two cycling cells or two non cycling cells. When combined with the observation of asymmetric partitioning of numb protein in some 2 cell clones (FIG. 4)[20,21], which marks asymmetric division in neural and myogenic precursors, we are led to conclude that planar-orientated division of EPCs produces may be either symmetric or asymmetric (a phenomenon also seen in Zebra Fish retinal precursors 22).

These observations are embodied in a model of clonal fate involving just three parameters: the overall division rate λ of proliferating (A-type) EPCs, the probability that the division is asymmetric $p_{AD}$, and the rate of transfer Γ of non proliferating (B-type) EPCs from the basal to the suprabasal layer. Further, to maintain a steady-state EPC population, one may note that the rates of symmetric cell division, A→A+A and A→B+B, must be equal. Finally, the observation that the number of basal layer cells/unit area remains constant (data not shown) leads to the additional constraint Γ=n/(1−n), where n denotes the volume fraction of EPCs in the basal layer, reducing the number of adjustable parameters to just two.

Formally, defining $P_{mn}(t)$ as the probability that a labelled clone involves m A-type EPCs and n B-type EPCs after a time t after induction, the time-evolution associated with the corresponding branching-annihilation process is specified by the Master equation, $$\frac{d}{dt}P_{mn} = \lambda\left\{\frac{1}{2}(1-p_{AD})[(m-1)P_{m-1,n}+(m+1)P_{m+1,n-2}]+p_{AD}mP_{mn-1}-mP_{mn}\right\}+\Gamma[(n+1)P_{mn+1}-nP_{mn}]$$

which must be solved subject to the initial condition $P_{mn}(0)=n\delta_{m1}\delta_{n0}+(1-n)\delta_{m0}\delta_{n1}$. Although the corresponding dynamics is integrable, the recovery of an analytic expression for the full distribution function seems infeasible. By contrast, the solution of the Master equation can be obtained straightforwardly by numerical integration.

Figure 5:
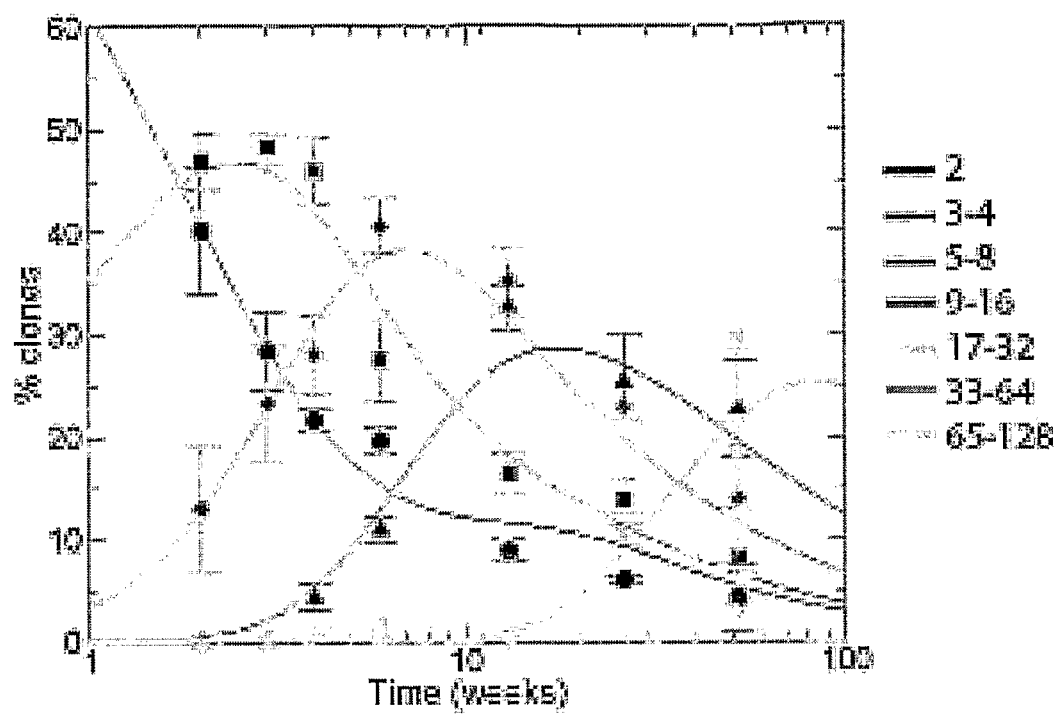
FIG. 5 shows the distribution of basal cells per clone for labelled clones containing 2 or more cells over 1 year post induction. Points with error bars (sem) are observed results, curves are predictions of EPC behaviour.
Figure 6:
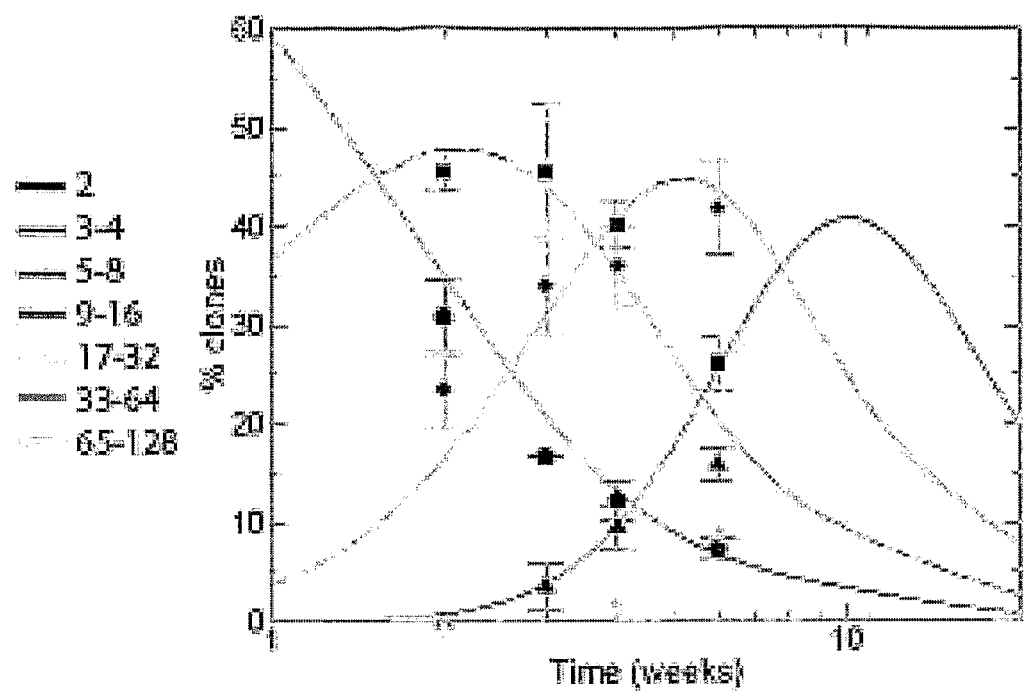
FIG. 6 shows the distribution of clone size (total cells per clone) over 6 weeks following induction. Points with error bars (sem) are observed results, curves are predictions of EPC generating the proportions of clones of the sizes shown.
Figure 7:
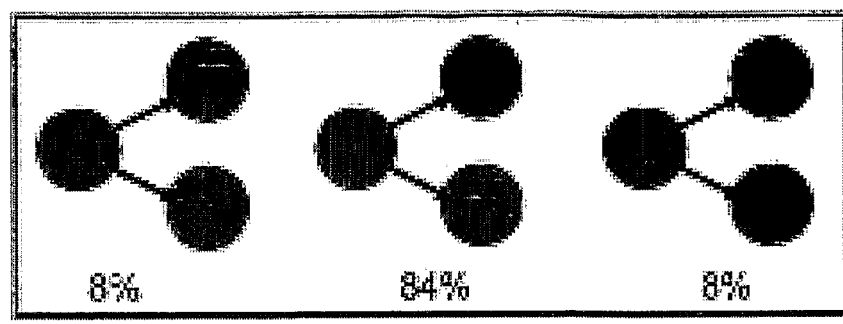
FIG. 7 shows a summary of EPC fate. EPC cell division generates either 2 cycling cells (light), a post mitotic basal cell (dark) and a cycling cell, or 2 post mitotic cells, with the frequencies shown and a mean cell division rate of once/week.

Taking the experimental value of n=0.15, a fit to the basal layer population (FIG. 7) shows good quantitative agreement with the experimental data for λ=1/week (implying Γ=0.2/week), and $p_{AD}$=0.84, i.e. 8% of EPC divisions generate two progenitor cells, 8% produce two post-mitotic cells, while the remaining 84% are asymmetric, a figure comparable to that found embryonic mouse epidermis.[18] Significantly, when applied to the total clone cell population (available up to six weeks), the same parameters provide a good quantitative fit to the data (FIG. 6). Moreover, a measurement of the percentage of two cell clones with two basal layer cells provides a means to discriminate between the different cell types (basal versus. suprabasal) (FIG. 5). In both cases (experiment and theory), one obtains a figure of 63%.

To further critically assess the basis of the model, and to demonstrate its predictive power, we have examined the effects of increasing the rate of epidermal proliferation and differentiation by treatment with retinoids. Two protocols were used: (1) Mice were induced and after a three month interval treated with either 0.33 mM all trans retinoic acid (ATRA) or vehicle alone for a further 3 months. (2) Mice were treated with 1 mM all trans retinoic acid (ATRA) or vehicle alone for 2 weeks, beginning immediately after induction. In both cases, clone size was seen to increase substantially in ATRA treated animals, in keeping with the increased proliferation rate assessed by Ki67 staining in ATRA treated mice (57.0+/−3.7% as compared with 16.5+/−2.2% (mean+/−sem) in controls. ATRA treatment did not alter the orientation of mitotic spindles (FIGS. 11 and 12). Significantly, in fitting the model to the observed two cell clone distribution at two weeks, we find that, in both protocols, the data are compatible with an AD rate of 84%, unchanged from the wildtype, while the EPC division rate is increased by a factor 1.4 in the vehicle and by 22 in the ATRA treated system (FIG. 8). Applied to the six month distribution, a comparison of the model prediction to the experimental data shows remarkable quantitative agreement (FIG. 8). A significant contribution of unlabelled cycling SC is thus incompatible with observed clonal behaviour in either normal and ATRA treated epidermis.

It has been suggested that only cells that persist in a tissue for an extended period have the potential to acquire the multiple mutations that give rise to cancer. These results herein show that
all cycling EPC have an equal probability of generating long lived clones susceptible to cancer causing mutations.

Example 2

Method

In this example a method of assessing the proliferation or differentiation behaviour of a population of target cells in a biological system is demonstrated.

In this example, the target cells are epidermis cells of a test mouse. A proportion of them are labelled with an inheritable marker at time t=0. In this example the cells are labelled as in example 1.

Next the value of at least one proliferation characteristic of said cells at least one time point t is measured, wherein said proliferation characteristic is the clone size distribution; In this example t is 4 weeks (4 weeks from labelling).

Next the clone size distribution measured above is compared to a reference clone size distribution at a corresponding time point t predicted or described by the equation;

$$\frac{dP_{n_A,n_B}}{dt} = $$
$$\lambda\{r[(n_A - 1)P_{n_A-1,n_B} + (n_A + 1)P_{n_A+1,n_B-2}] + (1 - 2r)n_A P_{n_A,n_B-1} - n_A P_{n_A,n_B}\} + \Gamma[(n_B + 1)P_{n_A,n_B+1} - n_B P_{n_A,n_B}]$$

In this example, the reference clone size distribution is generated by application of the above equation to clone sizes from normal mouse epidermis at corresponding time t.

A difference between the measured clone size distribution of the test mouse and the predicted or described clone size distribution of the reference cells indicates an altered proliferation or differentiation behaviour of said cells. In this example, no difference was found and so no altered behaviour of the cells in the test mouse was inferred.

Example 3

Derivation, Application and Scaling Studies

Overview

According to the current model of adult epidermal homeostasis, skin tissue is maintained by two discrete populations of progenitor cells: self-renewing stem cells; and their progeny, known as transit amplifying cells, which differentiate after several rounds of cell division[1-3]. By making use of inducible genetic labelling, we have tracked the fate of a representative sample of progenitor cells in mouse tail epidermis at single-cell resolution in vivo at time intervals up to one year. Here we show that clone-size distributions are consistent with a new model of homeostasis involving only one type of progenitor cell. These cells are found to undergo both symmetric and asymmetric division at rates that ensure epidermal homeostasis. The results enable insights into the role of stem cells on tissue maintenance in vivo.

Methods for Example 3

Animals and Sample Preparation

All animal experiments were conducted as specified by Home Office Project License. The generation of AhcreERT and R26$^{EYFP/EYFP}$ mice has been described previously[16,17]. When Ahcre$^{ERT}$ R26$^{EYFP/wt}$ mice are treated with multiple doses of βNF and tamoxifen, a high level of recombination was seen in the upper hair follicle and IFE (FIG. 18). The drug doses were titrated down to produce low-frequency labelling; a single intraperitoneal injection of 80 mg per kg β-naphthoflavone (Sigma-Aldrich) and 1 mg tamoxifen-free base (MP Biomedicals) dissolved in corn oil resulted in EYFP expression in approximately 1 in 600 basal cells of tail IFE and in 1 in 40 basal cells of back IFE, at 2 weeks post-induction[17]. No labelling was detected in the bulge region of the hair follicle and there was no background labelling in untreated Ahcre$^{ERT}$ R26$^{EYFP/wt}$ animals, even at 15 months of age (FIG. 18c, d). Epidermal wholemounts were prepared as described[18]. For analysis of back epidermis, 60-μm cryosections were used.

Immunostaining and Imaging

Immunostaining of wholemounts was performed as described[18]. The following primary antibodies were used; anti-GFP conjugated to AlexaFluor488 or 555 (Molecular Probes), anti-Ki67 (Abcam), anti-numb (Abcam), anti-cleaved caspase 3 (Cell Signalling Technology) and anti-α-tubulin conjugated to FITC (Sigma). Secondary antibodies were from Molecular Probes. Confocal images are presented as Z-stack projections; 30-120 optical sections in 0.2-2 μm increments were rendered using Improvision Volocity software.

Analysis of Clone Size, Number and Proliferation

Data presented is a typical example of at least two experiments with at least three mice per time point.

Tail Epidermis

The patterned organization of tail epidermis, enabled definition of a unit area of tail IFE between adjacent rows of hair follicles, which measured 282,000±2,300 μm$^2$ and contained 4,870±400 (mean±s.d.) basal-layer cells (FIG. 22a). The mean number of labelled clones per unit area of tail IFE was assessed by counting all clones detected by confocal imaging of 50 unit areas in each of three mice at each time point, except at 6 and 12 months when 100 areas were counted. Clone size was determined by Z-stack confocal imaging of at least 50 clones containing at least one basal cell in each mouse at each time point. We note that after 6 weeks anucleate cornified layer cells appeared in labelled clones, making it impossible to count total cell numbers; hence, the total number of cells per clone was counted up to 6 weeks, while the total number of basal cells could be scored up to one year. The percentage of Ki67-positive cells was determined by imaging at least 1,500 basal cells in multiple fields from at least three mice.

Back Skin Epidermis

60-μm cryosections were analysed by optical sectioning. To determine clone number, all clones in three 10-mm lengths of epidermis were analysed in each mouse at time points up to 3 months; at 6- and 12-month time points at least 5 cm of epidermis was scored for each mouse. The maximum clone diameter, expressed as number of basal cells, was scored for at least 50 clones in each of three mice at each time point.

Apoptosis

Wholemounts of tail epidermis from 2 days, 1 week, 2 weeks, 3 weeks, 4 weeks and 6 weeks after induction were stained with an anti-cleaved caspase3/AlexaFluor488 conjugate; positive Caspase 3 staining was confined to catagen hair follicles. In further experiments, staining for cleaved caspase 3 and apoptotic bodies, visualized by DAPI, was examined in the basal layer in wholemounts from mice at 3 weeks and 6 months post-induction. As a positive control, epidermal wholemounts were irradiated with 160 mJ cm$^{-2}$ UVC and analysed after a 16-hour incubation at 37° C.

Analysis of Mitotic Spindle Orientation

Wholemounts of DAPI-stained tail IFE were analysed by acquiring Z-stacks of all nuclei containing condensed chromosomes, as revealed by uniform, intense DAPI staining. Images were rendered in three dimensions, as above, and spindle orientation of all mitotic figures from metaphase to telophase was scored as described[22].

Analysis of cre Expression cre$^{ERt}$ messenger RNA levels after induction were analysed by quantitative polymerase chain reaction with reverse transcription (RT-PCR) of RNA prepared from tail epidermis using Trizol (Sigma). Primers used were 5'-CGTACTGACG-GTGGGAGAAT and 5'-CCCGGCAAAACAGGTAGTTA, and the product was detected using SyBr Green. GAPDH mRNA was measured with a Taqman probe (Applied Biosystems).

Flow Cytometry

A single-cell suspension was prepared from tail epidermis, using a 30 min incubation with Dispase II (Roche), followed by digestion with trypsin EDTA; this method separates the interfollicular epidermis from the dermis and lower hair follicles. After staining with biotin-conjugated anti-β1 integrin antibody (BD Biosciences/Pharmingen) and Alexa488-streptavidin (Molecular Probes), samples were fixed with paraformaldehyde, permeabilized with 0.1% saponin with 100 μml$^{-1}$ RNase A and 50 μg ml$^{-1}$ propidium iodide, and analysed on a BD Facscalibur flow cytometer, using propidium iodide channel pulse area/width gating to exclude cell doublets.

Background

The mammalian epidermis is organized into hair follicles interspersed with interfollicular epidermis (IFE), which consists of layers of keratinocytes (FIG. 14a)[4]. In IFE, proliferating epidermal progenitor cells (EPCs) are found in the basal cell layer. On commitment to terminal differentiation, basal cells exit the cell cycle and subsequently migrate into the suprabasal cell layers. Progenitors capable of generating both hair follicles and IFE lie in the hair-follicle bulge, but these cells appear to play no part in maintaining normal interfollicular epidermis[5-9]. Label-retaining studies show that IFE contains slowly cycling basal cells which have been interpreted as representing stem cells that support clonal units of transit amplifying (TA) and differentiated cells[10,11], according to the stem/TA cell hypothesis. However, these studies are unable to reveal the dynamics of EPC behaviour during epidermal homeostasis. Previous genetic labelling studies to track the fate of proliferating cells have either required epidermal injury or have yielded too few labelled clones to permit quantitative analysis[12-15].

Application to Epidermis

To track EPC fate in normal epidermis we have used inducible genetic marking to label a sample of cells and their progeny in adult mice. Animals transgenic for the tamoxifen-regulated mutant of cre recombinase (Ahcre$^{ERT}$), expressed from the inducible CYP1A1 promoter, were crossed onto the R26$^{EYFP/EYFP}$ reporter strain, in which a conditional allele of enhanced yellow fluorescent protein (EYFP) is targeted to the Rosa26 locus (FIG. 18a; refs 16, 17). In the resultant Ahcre$^{ERT}$ R26$^{EYFP/wt}$ heterozygotes, EYFP is expressed in a dose-dependent manner following transient expression of cre induced by a treatment with βNF and tamoxifen at 6-9 weeks of age (FIG. 18). Cohorts of mice were culled for analysis at intervals after a single injection of the inducing drugs. Cells expressing EYFP and their labelled progeny were detected by confocal microscopy of wholemount epidermis[18]. At 2 days post-induction, only singly labelled cells were seen, at a frequency of 1 in 600 cells in the basal layer, indicating that the clusters of cells encountered at later time points are clones, each derived from a single progenitor cell (FIG. 14b). Analysis of subsequent cohorts of mice demonstrated clones that remained cohesive and expanded progressively in size (FIG. 14b, FIG. 19). We scored clones that contained one or more basal cells, and the observed clone-size distribution (that is, the total number of nucleated cells per clone) up to 6 weeks post-labelling, and the basal-layer clone-size distribution up to one year (see Methods) are shown in FIG. 15.

The density of labelled clones containing at least one basal-layer cell in tail epidermis rose from 2 days to a peak at 2 weeks after induction, as EYFP levels accumulated to detectable levels in all labelled cells. Clone numbers then fell to 7±2% (mean±s.d.) of the peak value by 3 months, and 3±2% at one year; similar results were seen in back skin. This decline was accompanied by the appearance of multi-cellular clones containing only suprabasal cells, consistent with clonal loss through differentiation (FIG. 21). Analysis of spatial distribution of IFE clones indicates that labelled clones are not replaced by unlabelled clones migrating from hair follicles (FIG. 22). Moreover, none of the labelled clones can derive from bulge stem cells because this region is not labelled (FIG. 18 and below).

Before attempting to interpret the clone fate data, it is necessary to assess the extent to which they are influenced by tissue growth or apoptosis. First, the rate of increase in epidermal surface area due to growth was low (estimated at less than 3.5% per month over the time course of the experiment), whereas apoptosis was undetectable in basal-layer cells (see below and FIG. 23). Furthermore, the number of basal-layer cells per unit area and the proportion of cycling cells (as assessed both by Ki67 and cdc6 immunostaining) showed no significant difference between 2-week and one-year samples. Both techniques of assessing the proportion of cycling cells gave similar results, as did flow cytometry: 22±3% (mean±s.d.) for Ki67; 24±4% for cdc6; and 22±1% for flow cytometry (see FIG. 24)[19,20]. Finally, there was no significant difference between the proportion of cycling cells in the labelled and unlabelled cell populations, either at 5 days or one year post-induction (see below and FIG. 19). We therefore conclude that basal-layer cells labelled at induction are typical of the entire basal cell population, and that the observed clonal evolution is representative of the adult system in epidermal homeostasis.

According to the stem/TA cell hypothesis, TA cells undergo a limited number of cell divisions followed by differentiation[21]. To test this prediction, we examined clones at 3 weeks, over 90% of which are lost by 12 weeks post-induction. Significantly, clones comprising three or more cells contained both basal and suprabasal cells, indicative of asynchronous terminal differentiation (FIG. 16a). Furthermore, the immunostaining of clones consisting of two basal cells reveals that a single cell division may generate either one cycling and one non-cycling daughter, or two cycling daughters, or two non-cycling daughters (FIG. 16b). This raises the question of whether there is asymmetric cell division within the basal plane as described in the Drosophila peripheral nervous system and zebrafish retinal precursors[22,23]. Three-dimensional imaging of wholemount epidermis revealed that only 3% of mitotic spindles lie perpendicular to the basal layer, indicating that, in contrast to embryonic epidermis, the vast majority of EPC divisions generate two basal-layer cells (FIG. 25; refs 24, 25). The observation of asymmetric partitioning of numb protein (which marks asymmetric division in neural and myogenic precursors) in clones consisting of [ED: ie clones consisting of only 2 basal cells, not 2 basal cells+ suprabasal cells] two basal cells suggests that planar-orientated asymmetric division also occurs in the epidermis (FIG. 16c)[26,27]. EPC behaviour thus differs substantially from that observed in committed precursors in other systems[28,29].

We next considered the behaviour of the long-lived clones that persist for over 3 months. Within the stem/TA cell hypothesis, the epidermis is organized into epidermal proliferative units comprising about ten basal cells supported by a single self-renewing stem cell[11]. If individual stem cells retain their self-renewal capacity, the stem/TA cell model predicts that the basal-layer clone-size distribution must become time-independent and characteristic of a single epidermal proliferative unit. Such behaviour is in stark contrast to the progressive increase in average clone size observed in the epidermis (FIG. 15).

Faced with this apparent contradiction, we could attempt to revise the stem cell/TA cell model, but staying within the general paradigm. This might include introducing the capacity for stem-cell ageing and/or migration[15]. Alternatively, we could try to exploit the range of experimental data to seek evidence for a new paradigm for epidermal homeostasis. Intriguingly, such evidence is found in the scaling properties of the observed clone-size distribution. Here we argue that the clone fate data are compatible with a model in which ife is maintained by only one compartment of proliferating cells. Whether this model should be considered as an extreme variant of the stem/TA cell hypothesis or a new concept is arguably a matter of semantics, a point we will return to later.

To identify the scaling behaviour, we define the clone-size distribution $P_n(t)$, describing the probability that a labelled progenitor cell develops into a clone with a total of n basal-layer cells at time t after induction. From this we can define the distribution of 'persisting' clones, that is, the distribution of labelled clones containing at least one basal-layer cell:

$$P^{pers}_{n>0}(t) \equiv \frac{P_n(t)}{1 - P_0(t)}$$

With this definition, we show that (FIG. 17a and below), after an initial transient behaviour, the observed clone-size distributions are compatible with the simple scaling form:

$$P^{pers}_{n>0}(t) = \frac{\tau}{t} f(n\tau/t) \qquad (1)$$

where τ denotes some constant timescale. From this striking observation, we deduce that, at long times, the average number of basal-layer cells within a persisting clone increases linearly with time, a behaviour inconsistent with the existence of long-lived cycling stem cells. More significantly, the scaling indicates that long-time properties of clonal evolution are dictated by only one characteristic timescale r, consistent with a simple model of clonal fate in which external factors, such as stem-cell ageing or skin injury, do not have a significant impact.

Taken together, all of our experimental observations and the scaling behaviour are consistent with a model of clonal fate involving only one type of EPC and just three adjustable parameters: the overall division rate λ of proliferating (labelled A-type) EPCs; the proportion of cell divisions that are asymmetric, (1−2r); and the rate of transfer Γ of non proliferating (B-type) cells from the basal to the suprabasal layer (see schematic in FIG. 17b). To maintain a steady-state EPC population, the rates of symmetric cell division, A→A+A and A→B+B, must be identical and equal to r. Finally, the observation that the basal-layer cell density remains constant leads to the additional constraint Γ=λρ/(1−ρ), where ρ denotes the proportion of proliferating cells in the basal layer, reducing the number of adjustable parameters to just two.

Defining $P_{n_A,n_B}(t)$ as the probability that a labelled clone involves $n_A$ A-type and $n_B$ B-type EPCs at time t after induction, its time-evolution is governed by the Master equation:

$$\frac{dP_{n_A,n_B}}{dt} = \lambda\{r[(n_A-1)P_{n_A-1,n_B} + (n_A+1)P_{n_A+1,n_B-2}] + (1-2r)n_A P_{n_A,n_B-1} - n_A P_{n_A,n_B}\} + \Gamma[(n_B+1)P_{n_A,n_B+1} - n_B P_{n_A,n_B}]$$

subject to the initial condition $P_{n_A,n_B}(0) = \rho \delta_{n_A,1}\delta_{n_B,0} + (1-\rho)\delta_{n_A,0}\delta_{n_B,1}$. Although an exact analytical solution to this equation is unavailable, at times t>1/rλ the system enters an asymptotic regime where, defining $n=n_A+n_B$, we may show that the basal-layer clone-size distribution for persisting clones acquires the observed scaling form in equation (1) with $f(x)=e^{-x}$ and τ=ρ/rλ; that is, the long-time properties of clonal evolution are dictated by the symmetric division rate, rλ. When combined with the experimentally inferred value for the fraction of proliferating basal-layer cells ρ=0.22, a fit of the data to the asymptotic distribution (FIG. 17a, inset) identifies 1.2=0.088±0.004 per week.

At times t<1/rλ≈11 weeks, the transient behaviour of the basal-layer clone-size distribution dominates. In this regime, both the basal-layer and total clone-size distributions can be determined from a numerical integration of the corresponding Master equation. Taking rλ from the asymptotic data dependence, a one-parameter fit of the basal-layer clone-size distribution to the experimental data obtains a good quantitative agreement over the entire one-year time course for r=0.08 (FIG. 15d), that is EPC division takes place at a rate of 2=1.1 per week (a figure consistent with previous estimates[21]), with 84% of divisions resulting in asymmetric fate, while the cell transfer rate out of the basal layer takes place at a rate of r=0.31 per week. With the same choice of parameters, the total clone-size distribution also shows a striking quantitative agreement with experiment (FIG. 15b). It should be noted that the slow accumulation of labelled clones over the 2 weeks following induction has no significant effect on the fit of the model.

In conclusion, we have shown that the entire range of clonal fate data reported here is compatible with a model involving a single proliferating cell compartment in mouse tail skin epidermis.

A similar analysis in back skin was carried out using changes in clone diameter as a measure of clone size. Cell behaviours observed at this site are in qualitative agreement with a single-compartment model. It may be noted that, if present, a small quiescent population of stem cells would be undetectable in our analysis, but would be expected to be highly active in processes such as wound healing[8]. Previous models of epidermal homeostasis hypothesize the existence of a TA cell compartment, which undergoes a limited number of divisions. We show that tail epidermis is maintained by a single population of progenitor cells, which may undergo an unlimited number of divisions.

References to Example 3

1. Lajtha, L. G. Stem cell concepts. Differentiation 14, 23-34 (1979).
2. Alonso, L. & Fuchs, E. Stem cells of the skin epithelium. Proc. Natl Acad. Sci. USA 100 (suppl. 1), 11830-11835 (2003).
3. Braun, K. M. & Watt, F. M. Epidermal label-retaining cells: background and recent applications. J. Invest. Dermatol. Symp. Proc. 9, 196-201 (2004).
4. Gambardella, L. & Barrandon, Y. The multifaceted adult epidermal stem cell. Curr. Opin. Cell Biol. 15, 771-777 (2003).
5. Tumbar, T. et al. Defining the epithelial stem cell niche in skin. Science 303, 359-363 (2004).
6. Morris, R. J. et al. Capturing and profiling adult hair follicle stem cells. Nature Biotechnol. 22, 411-417 (2004).
7. Levy, V., Lindon, C., Harfe, B. D. & Morgan, B. A. Distinct stem cell populations regenerate the follicle and interfollicular epidermis. Dev. Cell 9, 855-861 (2005).
8. Ito, M. et al. Stem cells in the hair follicle bulge contribute to wound repair but not to homeostasis of the epidermis. Nature Med. 11, 1351-1354 (2005).
9. Claudinot, S., Nicolas, M., Oshima, H., Rochat, A. & Barrandon, Y. Long-term renewal of hair follicles from clonogenic multipotent stem cells. Proc. Natl Acad. Sci. USA 102, 14677-14682 (2005).
10. Mackenzie, I. C. Relationship between mitosis and the ordered structure of the stratum corneum in mouse epidermis. Nature 226, 653-655 (1970).
11. Potten, C. S. The epidermal proliferative unit: the possible role of the central basal cell. Cell Tissue Kinet. 7, 77-88 (1974).
12. Ghazizadeh, S. & Taichman, L. B. Multiple classes of stem cells in cutaneous epithelium: a lineage analysis of adult mouse skin. EMBO J. 20, 1215-1222 (2001).
13. Kameda, T. et al. Analysis of the cellular heterogeneity in the basal layer of mouse ear epidermis: an approach from partial decomposition in vitro and retroviral cell marking in vivo. Exp. Cell Res. 283, 167-183 (2003).
14. Ro, S. & Rannala, B. A stop-EGFP transgenic mouse to detect clonal cell lineages generated by mutation. EMBO Rep. 5, 914-920 (2004).
15. Ro, S. & Rannala, B. Evidence from the stop-EGFP mouse supports a niche-sharing model of epidermal proliferative units. Exp. Dermatol. 14, 838-843 (2005).
16. Srinivas, S. et al. Cre reporter strains produced by targeted insertion of EYFP and ECFP into the ROSA26 locus. BMC Dev. Biol. 1, 4 (2001).
17. Kemp, R. et al. Elimination of background recombination: somatic induction of Cre by combined transcriptional regulation and hormone binding affinity. Nucleic Acids Res. 32, e92 (2004).
18. Braun, K. M. et al. Manipulation of stem cell proliferation and lineage commitment: visualisation of label-retaining cells in wholemounts of mouse epidermis. Development 130, 5241-5255 (2.003).
19. Williams, G. H. et al. Improved cervical smear assessment using antibodies against proteins that regulate DNA replication. Proc. Natl Acad. Sci. USA 95, 14932-14937 (1998).
20. Birner, P. et al. Immunohistochemical detection of cell growth fraction in formalin-fixed and paraffin-embedded murine tissue. Am. J. Pathol. 158, 1991-1996 (2001).
21. Potten, C. S. Cell replacement in epidermis (keratopoiesis) via discrete units of proliferation. Int. Rev. Cytol. 69, 271-318 (1981).
22. Das, T., Payer, B., Cayouette, M. & Harris, W. A. In vivo time-lapse imaging of cell divisions during neurogenesis in the developing zebrafish retina. Neuron 37, 597-609 (2003).
23. Gho, M. & Schweisguth, F. Frizzled signalling controls orientation of asymmetric sense organ precursor cell divisions in Drosophila. Nature 393, 178-181 (1998).
24. Lechler, T. & Fuchs, E. Asymmetric cell divisions promote stratification and differentiation of mammalian skin. Nature 437, 275-280 (2005).
25. Smart, I. H. Variation in the plane of cell cleavage during the process of stratification in the mouse epidermis. Br. J. Dermatol. 82, 276-282 (1970).
26. Zhong, W., Feder, J. N., Jiang, M. M., Jan, L. Y. & Jan, Y. N. Asymmetric localization of a mammalian numb homolog during mouse cortical neurogenesis. Neuron 17, 43-53 (1996).
27. Conboy, I. M. & Rando, T. A. The regulation of Notch signaling controls satellite cell activation and cell fate determination in postnatal myogenesis. Dev. Cell 3, 397-409 (2002).
28. Smart, F. M. & Venkitaraman, A. R. Inhibition of interleukin 7 receptor signaling by antigen receptor assembly. J. Exp. Med. 191, 737-742 (2000).
29. Temple, S. & Raff, M. C. Clonal analysis of oligodendrocyte development in culture: evidence for a developmental clock that counts cell divisions. Cell 44, 773-779 (1986).

Example 4

Application to Different Tissues and Additional Techniques

Analysis of epidermal wholemounts and sections: Tail epidermis. The patterned organisation of tail epidermis, enabled definition of a unit area of tail IFE between adjacent rows of hair follicles which measured 282,000+/−2300 µm$^2$ and contained 4870+/−400 (mean+/−SD) basal layer cells (FIG. 22a). The mean number of labelled clones per unit area of tail IFE was assessed by counting all clones detected by confocal imaging of 50 unit areas in each of three mice at each time point, except at 6 and 12 months when 100 areas were counted. Clone size was determined by Z stack confocal imaging of at least 50 clones containing at least one basal cell in each mouse at each time point. Note that, after 6 weeks anucleate cornified layer cells appear in labelled clones making it impossible to count total cell numbers; hence, the total number of cells per clone was counted up to 6 weeks, while the total number of basal cells could be scored up to 1 year. The percentage of Ki67 positive cells was determined by imaging at least 1500 basal cells in multiple fields from at least 3 mice. Back skin epidermis. 60 µm cryosections were analysed by optical sectioning. To determine clone number, all clones in three 10 mm lengths of epidermis were analysed in each mouse at time points up to 3 months; at 6 and 12 month time points at least 5 cm of epidermis was scored for each mouse. The maximum clone diameter, expressed as number of basal cells, was scored for at least 50 clones in each of 3 mice at each time point.

Apoptosis. Wholemounts of tail epidermis from 2 days, 1 week, 2 weeks, 3 weeks, 4 weeks and 6 weeks after induction were stained with an anti-cleaved caspase3/AlexaFluor488 conjugate; positive Caspase 3 staining was confined to catagen hair follicles. In further experiments, staining for cleaved caspase 3 and apoptotic bodies, visualised by DAPI, was examined in the basal layer in wholemounts from mice at 3 weeks and 6 months post induction. As a positive control epidermal wholemounts were irradiated with 160 mJ/cm2 UVC and analysed after a 16 hour incubation at 37 C.

Analysis of Mitotic Spindle Orientation. Wholemounts of DAPI stained tail IFE were analysed by acquiring Z stacks of all nuclei containing condensed chromosomes, as revealed by uniform, intense DAPI staining. Images were rendered in 3 dimensions, as above, and spindle orientation of all mitotic figures from metaphase to telophase scored as described[22].

Analysis of cre expression. $cre^{ERt}$ mRNA levels following induction were analysed by quantitative RT-PCR of RNA prepared from tail epidermis using Trizol (Sigma). Primers used were 5' CGTACTGACGGTGGGAGAAT and 5' CCCGGCAAAACAGGTAGTTA, and the product was detected using SyBr green. GAPDH mRNA was measured with a Taqman probe (Applied Biosystems).

Flow cytometry. A single cell suspension was prepared from tail epidermis, using a 30 minute incubation with Dispase II (Roche) followed by digestion with trypsin EDTA; this method separates the interfollicular epidermis from the dermis and lower hair follicles. After staining with biotin conjugated anti β1 integrin antibody (BD Biosciences/Pharmingen) and Alexa488-streptavidin (Molecular Probes) samples were fixed with paraformaldehyde, permeabilised with 0.1% saponin with 100 µg/ml RNAse A and 50 µg/ml propidium iodide (PI) analysed on a BD Facscalibur flow cytometer, using PI channel pulse area/width gating to exclude cell doublets.

Characterisation of $Ahcre^{ERt}$ Induced EYFP Expression.

It was important to determine the duration of $cre^{ERt}$ expression following induction, to determine the interval over which labelling would occur. Mice were induced with a single injection of βNF and tamoxifen and the level of $cre^{ERt}$ mRNA in tail skin epidermis assayed by real time RT-PCR at baseline and at 24 and 48 hours post induction. $Cre^{RRt}$ transcriptrises at 24 hours but returns to background levels by 48 hours (FIG. 18b).

The location of labelled cells was then assessed. After induction labelling was detected in single cells in interfollicluar epidermis, sebaceous glands and the upper hair follicle. Of 2870 hair follicles containing labelled clones at 1 year, all clones were confined to the upper hair follicle; in no case was EYFP detected in the bulge or lower follicle (FIG. 18d,e and data not shown). This is significant in view of the localisation of multipotential stem cells in the hair follicle bulge[1,2].

We also analysed the dose responsiveness of the EYFP promoter. Mice were induced to the maximum tolerated dose of βF and tamoxifen. The level of labelling in epidermis analysed 5 days later was dramatically increased compared with a single inducing injection, but was confined to the same regions of the epidermis and hair follicle as label at lower doses (FIG. 18e). Furthermore, confluent labelling of patches of basal cells, over 30 cells in size was detected (FIG. 18f).

We also investigated whether there was a background rate of recombination in the absence of inducing drugs. We were unable to detect any EYFP expression in tail wholemounts of uninduced animals at 15 months of age by either confocal microscopy or flow cytometry.

Proliferation in Labelled and Unlabelled Cells

To further address the issue of whether labelled clones were representative of all basal cells, we determined the proportion of proliferating cells in the maximally induced mice, given daily injections of βF and tamoxifen for 5 days and analysed at 10 days after the first injection (FIG. 18 e,f and data not shown). The percentages of Ki67positive cells in the labelled and unlabelled cell populations were 22+/−2.5%, (mean+/−SD) and 22+/−1% respectively.

The percentage of Ki67 positive basal cells was also the same in labelled clones, (20+/−4%, mean+/−SD) and adjacent unlabelled epidermis (20+/−5%) at 1 year after induction with a single injection of βNF and tamoxifen (FIG. 19).

Taken together this data indicates that the cells contained within labelled clones are representative of all EPC at both early and late time points (data not shown).

Differentiation of Basal Cell Containing Clones

We speculated that rapid loss of clones containing basal cells over the first 12 weeks of the experiment may be due to differentiation of all the basal cells within a clone, resulting in multicellular clones consisting entirely of suprabasal cells. To investigate if this was the case, epidermal wholemounts were examined at 2 days, and 2, 3 6 and 12 weeks post induction and multicellular clones were counted. The proportion of clones consisting only of suprabasal cells rose to a peak at 3 weeks, and fell to a low level by 12 weeks (FIG. 21). This is consistent with clones containing basal cells differentiating and leaving the basal layer, followed by loss of clones containing only suprabasal cells by shedding.

Expansion of Epidermal Surface Area with Age

To determine the relationship between age and epidermal surface area in tail epidermis, the tail length and diameter (at 2 cm from its base) was measured in $Ahcre^{ERT}$ $R26^{EYFP/wt}$ mice or mice of an identical SV129/C57BL6 background in animals from 6 weeks to 8.5 months of age (FIG. 23). In both cases, over the time course of the experiment, there was no significant change in tail length with age. In both male and female mice, the tail diameter, d, varied linearly with age such that:

$$d(t)=29 \text{ mm}+(t/\text{month})\times 1.0 \text{ mm in males } (R^2=0.91, n=29),$$

and $$d(t)=30 \text{ mm}+(t/\text{month})\times 0.5 \text{ mm in females } (R^2=0.90, n=32).$$

As tail length is constant, the surface area of the tail must vary in proportion to the diameter increasing by 3%/month in males and 2%/month in females. Such a growth rate would not impact significantly on the observed clone size distributions.

To estimate the increase in body surface area with age we measured the body mass in the same group of animals (FIG. 23). In adult mice, the body mass, M, was found to scale logarithmically with age with a fit to the data of $$M = 14.7 \text{ g} + \ln(t/\text{month}) \times 7.8 \text{ g in males } (R^2=0.98, n=29),$$

and $$M = 13.2 \text{ g} + \ln(t/\text{month}) \times 14.6 \text{ g in females } (R^2=0.91, n=32)$$

If we assume that body mass is proportional to the volume of the mouse, the surface area must scale in proportion to $M^{2/3}$. Therefore, from six weeks to one year (i.e. over the total time course of the experiment), the surface area of the body of the mouse increases by approximately 50% in males and 88% in females. While such effects would not significantly influence the qualitative behaviour of labelled back skin clones, they could impact on a detailed quantitative analysis of the long-time properties of the clone size distribution in back skin. These factors should be borne in mind when applying quantitative modelling to back skin data.

Frequency of Apoptosis in Interfollicular Epidermis

To determine the frequency of apoptosis in the basal layer of interfollicular epidermis, we examined epidermis at 3 weeks and 6 months post induction for apoptotic bodies by DAPI staining and expression of caspase 3. The basal layer in 10 unit areas, each containing 4870±400 (mean±SD) cells (see FIG. 23), was examined for cleaved caspase 3 staining; no positive cells were found. Over 13,000 DAPI stained cells were examined for evidence of apoptotic bodies and none were found (FIG. 23 and table S1). In contrast, cleaved caspase 3 staining and apoptotic bodies were widespread in positive control wholemounts examined 16 hours after 120 mJ/cm$^2$ UVC irradiation.

These results are consistent with previous reports that the frequency of apoptotic cells in the epidermis of C57Bl6 mice is 0.02%, although this figure includes basal and suprabasal layer cells[3]. The rate of clearance of apoptotic cells is between 6-8 hours following UVB irradiation. If we assume that apoptotic cells in the basal layer are cleared at the same rate, we may conclude that the apoptotic rate in the basal layer of normal epidermis is less than 60 cells per million/day for cleaved caspase 3 positive cells, and 200 cells per million/day for apoptotic bodies. Over a one year time course, this translates to a predicted attrition due to apoptosis of less than 3% of the basal layer cells for cleaved caspase 3 positive cells and 10% for apoptotic bodies. Such effects would not impact significantly on the observed clone size distributions and could not explain the magnitude of the inexorable increase in average clone size observed in the tail skin data.

References to Example 4

1. Morris, R. J. et al. Capturing and profiling adult hair follicle stem cells. *Nat Biotechnol* 22, 411-7 (2004).
2. Tumbar, T. et al. Defining the epithelial stem cell niche in skin. *Science* 303, 359-63 (2004).
3. Lu, Y. P., Lou, Y. R., Peng, Q. Y., Xie, J. G. & Conney, A. H. Stimulatory effect of topical application of caffeine on UVB-induced apoptosis in the epidermis of p53 and Bax knockout mice. *Cancer Res* 64, 5020-7 (2004).

REFERENCES

1. Adami, J. G. The causation of cancerous and other new growths. British Medical Journal i, 621-628 (1901).
2. Lajtha, L. G. Stem cell concepts. *Differentiation* 14, 23-34 (1979).
3. Alonso, L. & Fuchs, E. Stem cells of the skin epithelium. *Proc Natl Acad Sci USA* 100 Suppl 1, 11830-5 (2003).
4. Braun, K. M. & Watt, F. M. Epidermal label-retaining cells: background and recent applications. *J Investig Dermatol Symp Proc* 9, 196-201 (2004).
5. Potten, C. S. The epidermal proliferative unit: the possible role of the central basal cell. *Cell Tissue Kinet* 7, 77-88 (1974).
6. Gambardella, L. & Barrandon, Y. The multifaceted adult epidermal stem cell. *Curr Opin Cell Biol* 15, 771-7 (2003).
7. Oshima, H., Rochat, A., Kedzia, C., Kobayashi, K. & Barrandon, Y. Morphogenesis and renewal of hair follicles from adult multipotent stem cells. *Cell* 104, 233-45 (2001).
8. Tumbar, T. et al. Defining the epithelial stem cell niche in skin. *Science* 303, 359-63 (2004).
9. Morris, R. J. et al. Capturing and profiling adult hair follicle stem cells. *Nat Biotechnol* 22, 411-7 (2004).
10. Levy, V., Lindon, C., Harfe, B. D. & Morgan, B. A. Distinct stem cell populations regenerate the follicle and interfollicular epidermis. *Dev Cell* 9, 855-61 (2005).
11. Ito, M. et al. Stem cells in the hair follicle bulge contribute to wound repair but not to homeostasis of the epidermis. *Nat Med* 11, 1351-4 (2005).
12. Mackenzie, I. C. Relationship between mitosis and the ordered structure of the stratum corneum mouse epidermis. *Nature* 226, 653-5 (1970).
13. Schmidt, G. H., Blount, M. A. & Ponder, B. A. Immunochemical demonstration of the clonal organization of chimaeric mouse epidermis. *Development* 100, 535-41 (1987).
14. Braun, K. M. et al. Manipulation of stem cell proliferation and lineage commitment: visualisation of label-retaining cells in wholemounts of mouse epidermis. *Development* 130, 5241-55 (2003).
15. Srinivas, S. et al. Cre reporter strains produced by targeted insertion of EYFP and ECFP into the ROSA26 locus. *BMC Dev Biol* 1, 4 (2001).
16. Kemp, R. et al. Elimination of background recombination: somatic induction of Cre by combined transcriptional regulation and hormone binding affinity. *Nucleic Acids Res* 32, e92 (2004).
17. Birner, P. et al. Immunohistochemical detection of cell growth fraction in formalin-fixed and paraffin-embedded murine tissue. *Am J Pathol* 158, 1991-6 (2001).
18. Lechler, T. & Fuchs, E. Asymmetric cell divisions promote stratification and differentiation of mammalian skin. *Nature* 437, 275-80 (2005).
19. Smart, I. H. Variation in the plane of cell cleavage during the process of stratification in the mouse epidermis. *Br J Dermatol* 82, 276-82 (1970).
20. Zhong, W., Feder, J. N., Jiang, M. M., Jan, L. Y. & Jan, Y. N. Asymmetric localization of a mammalian numb homolog during mouse cortical neurogenesis. *Neuron* 17, 43-53 (1996).
21. Conboy, I. M. & Rando, T. A. The regulation of Notch signaling controls satellite cell activation and cell fate determination in postnatal myogenesis. *Dev Cell* 3, 397-409 (2002).
22. Das, T., Payer, B., Cayouette, M. & Harris, W. A. In vivo time-lapse imaging of cell divisions during neurogenesis in the developing zebrafish retina. *Neuron* 37, 597-609 (2003).

Sequence Listing
Primer (SEQ ID NO:1)
5'-CGTACTGACGGTGGGAGAAT
Primer (SEQ ID NO: 2)
5' CCCGGCAAAACAGGTAGTTA

---

---

The invention claimed is:

1. A method of assessing the proliferation or differentiation behaviour of a population of target cells in a biological system, said method comprising the steps of;
   [a] measuring the value of at least one proliferation characteristic of said cells at least one time point t, wherein said proliferation characteristic is the clone size distribution;
   [b] comparing the clone size distribution measured in [a] to a reference clone size distribution at a corresponding time point t predicted or described by the equation;

$$\frac{dP_{n_A,n_B}}{dt} = \lambda\{r[(n_A - 1)P_{n_A-1,n_B} + (n+1)P_{n_A+1,n_B-2}] + (1 - 2r)n_A P_{n_A,n_B-1} - n_A P_{n_A,n_B}\} + r[(n_B + 1)P_{n_A,n_B+1} - n_B P_{n_A,n_B}]$$

wherein a difference between the measured clone size distribution of [a] and the predicted or described clone size distribution of [b] indicates an altered proliferation or differentiation behaviour of said cells.

2. A method according to claim 1 wherein said measurement and comparison steps are performed for two or more time points.

3. A method according to claim 1 wherein the clone size is determined as the number of cells in the clone.

4. A method according to claim 1 wherein the biological system is a tissue.

5. A method according to claim 4 wherein the tissue is epidermis.

6. A method according to claim 4 wherein the population of target cells is in a non-human test animal.

7. A method according to claim 1 wherein the population of cells consists of one or more clonal cell lineage(s).

8. A method according to claim 1 wherein said target cells are labelled with an inheritable marker.

9. A method according to claim 8 wherein fewer than 1 in 27 cells in the system are labelled as target cells.

10. A method according to claim 8 wherein the target cells are labelled by expression of a marker gene.

11. A method according to claim 10 wherein the value of at east one proliferation characteristic is measured by
   (i) providing a test animal comprising a marker gene,
   (ii) inducing inheritable activation of said marker in at least one cell of said test animal, wherein inheritable activation is induced in fewer than 1 in 27 cells in the tissue of interest,
   (iii) incubating the test animal,
   (iv) visualising those clonal cells which express the marker gene as a result of the inheritable activation, and
   (v) measuring the value of the at least one proliferation characteristic of the visualised clonal cells.

12. A method according to claim 11 wherein the visualisation is by confocal microscopy.

13. A method according to claim 1 wherein the target cells are treated with a test compound before the at least one proliferation characteristic is measured.

14. A method according to claim 13 wherein the target cells are comprised in the epidermis of a test animal and test compound is topically administered to the epidermis of the test animal.

15. A method according to claim 13 wherein a difference in the proliferation or differentiation characteristic(s) of the treated target cells relative to the reference cells is indicative that the test compound affects cell proliferation or differentiation behaviour.

16. A method according to claim 1 comprising expressing a test gene in the target cells before the at least one proliferation characteristic is measured.

17. A method according to claim 16 wherein increased proliferative behaviour of the target cells expressing the test gene is indicative that the test gene is an oncogene.

18. A method according to claim 1 comprising expressing a gene which changes growth behaviour in the target cells and treating the target cells expressing said gene with a test compound before the at least one proliferation characteristic is measured.

19. A method according to claim 18 wherein a reduction or enhancement of the changes in the growth behaviour induced by expression of said gene in the treated cells is indicative that the test compound affects cell growth behaviour.

20. A method according to claim 18 wherein expression of said gene increases proliferation in the target cells, and a reduction or abrogation of said proliferation in the treated cells is indicative that the test compound is a candidate cosmetic agent or anti-cancer therapeutic agent.

21. A method according to claim 1 wherein the target cells are deficient in p53.

22. A method according to claim 1 wherein the reference clone size distribution of (b) is a clone size distribution at a second time point t2 for a population of said target cells, said method further comprising
    (c) rescaling the clone size distributions to the same time co-ordinate; and
    (d) comparing the curve shapes of (c);
    wherein if said curve shapes are different, then the proliferation or differentiation behaviour of the cells is assessed to be abnormal.

23. A method according to claim 22 further comprising determining whether the proliferation or differentiation behaviour of the cells complies with the scaling form:

$$P_{n>0}^{pers}(t) = \frac{r}{t} f(nr/t)$$

wherein if said proliferation or differentiation behaviour conforms to said scaling form, then the proliferation or differentiation behaviour of the cells is assessed to be normal, and wherein if said proliferation or differentiation behaviour does not conform to said scaling form, then the proliferation or differentiation behaviour of the cells is assessed to be abnormal.

24. A method according to claim 1, said method further comprising;
    comparing at least one further parameter predicted or described by application of said equation to said target cell population with at least one further parameter predicted or described by application of said equation to said reference cell population; and
    identifying parameters which are altered in said target cell population; thereby characterising the changes in the proliferation or differentiation behaviour of the target cells.

* * * * *